United States Patent
Legrandjacques et al.

(10) Patent No.: US 6,419,387 B1
(45) Date of Patent: Jul. 16, 2002

(54) METHOD AND DEVICE FOR THE INSPECTION OF A MATERIAL BY THERMAL IMAGING

(75) Inventors: Laurent Legrandjacques, Dijon; Christophe Dehan, Le Mans; Jean-Claude Krapez, Chatillon; Francois Le Poutre, Janvry, all of (FR)

(73) Assignees: Framatome, Courbevoie; Office National d'Etudes et de Recherches Aerospatiales "Onera", Chatillon, both of (FR)

( * ) Notice: Subject to any disclaimer, the term of this patent is extended or adjusted under 35 U.S.C. 154(b) by 0 days.

(21) Appl. No.: 09/380,547
(22) PCT Filed: Mar. 4, 1998
(86) PCT No.: PCT/FR98/00429
§ 371 (c)(1), (2), (4) Date: Jan. 31, 2000
(87) PCT Pub. No.: WO98/39640
PCT Pub. Date: Sep. 11, 1998

(30) Foreign Application Priority Data

Mar. 5, 1997 (FR) .............................. 97 02620

(51) Int. Cl.$^7$ .......................... G01N 25/72; G02B 1/00
(52) U.S. Cl. .................. 374/5; 250/341.6; 250/332; 250/334; 374/57
(58) Field of Search ................ 374/5, 18, 22, 374/29, 30, 161, 57, 4, 45, 124, 137; 250/341.6, 332, 334

(56) References Cited

U.S. PATENT DOCUMENTS 3,808,439 A * 4/1974 Renius ................ 250/334
3,842,277 A * 10/1974 Jayachandra ............. 250/338
3,949,225 A * 4/1976 Aguilera .................. 250/334

(List continued on next page.)

FOREIGN PATENT DOCUMENTS

| GB | 2168494 | * 6/1986 | ............... 374/5 |
| JP | 62127660 | * 6/1986 | ............... 374/4 |
| WO | WO 87/00632 | 1/1987 | |

OTHER PUBLICATIONS

Non–destructive examination of fibre composite structures by thernal field techniques. McLaughlin et al. NDT ilnternational, 1980.*

Primary Examiner—Diego Gutierrez
Assistant Examiner—Gail Verbitsky
(74) Attorney, Agent, or Firm—Connolly Bove Lodge & Hutz LLP

(57) ABSTRACT

A heating zone (22) and a detection zone (23) at the surface (1a) of a part (1) are displaced in such a way as to carry out the scanning of the surface (1a) and a flux radiated in the detection zone (23) is detected by using a line of detectors (21) which is chosen from a matrix of detectors (20). The method makes is possible in particular to reduce the time for scanning the surface (1a) of the part and to be able to adjust the offset, in the direction of displacement (24), between the heating zone (22) and the detection (23), simply by choosing the line (21) of the matrix of detectors (20). The method and the device in accordance with the invention make it possible in particular to carry out thermographic inspections of parts made of any materials and in particular of metal parts which may have considerable dimensions and complex shapes.

15 Claims, 20 Drawing Sheets

U.S. PATENT DOCUMENTS

| | | | | |
|---|---|---|---|---|
| 3,989,946 A | * | 11/1976 | Chapman et al. | 250/332 |
| 4,080,532 A | * | 3/1978 | Hopper | 250/332 |
| 4,429,330 A | * | 1/1984 | Chapman | 358/113 |
| 4,703,179 A | * | 10/1987 | Motooka | 250/334 |
| 4,707,605 A | | 11/1987 | Astheimer et al. | 250/347 |
| 4,792,168 A | * | 12/1988 | Hanson | 250/338.2 |
| 4,792,683 A | * | 12/1988 | Chang et al. | 250/341 |
| 4,860,224 A | * | 8/1989 | Cashell et al. | 364/551.01 |
| 4,875,175 A | * | 10/1989 | Egee et al. | 364/551.01 |
| 4,900,367 A | * | 2/1990 | Gergis | 136/201 |
| 4,910,401 A | * | 3/1990 | Woods | 250/332 |
| 4,956,686 A | * | 9/1990 | Borrello et al. | 357/30 |
| 4,965,451 A | | 10/1990 | Sölter | 250/330 |
| 4,989,086 A | * | 1/1991 | Schaff et al. | 358/109 |
| 5,111,048 A | * | 5/1992 | Devitt et al. | 250/342 |
| 5,131,758 A | * | 7/1992 | Heyman et al. | 374/5 |
| 5,164,583 A | * | 11/1992 | Aichinger et al. | 250/214 VT |
| 5,246,291 A | * | 9/1993 | Lebeau et al. | 374/5 |
| 5,302,824 A | * | 4/1994 | Prager | 250/252.1 |
| 5,309,230 A | * | 5/1994 | Blondel et al. | 348/164 |
| 5,402,168 A | * | 3/1995 | Fouilloy | 348/164 |
| 5,460,451 A | * | 10/1995 | Wadman | 374/126 |
| 5,574,712 A | * | 11/1996 | Alon et al. | 369/102 |
| 5,582,485 A | * | 12/1996 | Lesniak | 374/5 |
| 5,654,977 A | * | 8/1997 | Morris | 374/4 |
| 5,667,300 A | * | 9/1997 | Mandelis et al. | 374/43 |
| 5,709,469 A | * | 1/1998 | White et al. | 374/5 |
| 5,711,603 A | * | 1/1998 | Ringermacher et al. | 374/5 |
| 5,740,272 A | * | 4/1998 | Shimada | 382/149 |
| 5,971,608 A | * | 10/1999 | Koizumi | 374/5 |
| 6,000,844 A | * | 12/1999 | Cramer et al. | 374/5 |
| 6,013,915 A | * | 1/2000 | Watkins | 250/341.1 |
| 6,049,220 A | * | 4/2000 | Borden et al. | 324/765 |
| 6,054,868 A | * | 4/2000 | Borden et al. | 324/752 |

* cited by examiner

METHOD AND DEVICE FOR THE INSPECTION OF A MATERIAL BY THERMAL IMAGING

The invention relates to a method and a device for the photothermal inspection of a material.

Photothermal inspection methods and devices are known which make it possible for example to effect the non-destructive testing of parts, so as to detect defects, variations in the nature or properties of the material of the part or differences in thickness of a coating layer of the part. These methods and devices may also be used to characterize local variations in diffusivity or in thermal conductivity at the surface or beneath the surface of a part made of the material. The part under inspection can be metallic and consist of a ferrous material, for example an alloy steel such as a stainless steel, or else of a non-ferrous material. The material may also be a composite, a ceramic material or a plastic.

The method of photothermal inspection which is carried out on a part or sample of material to be inspected uses the phenomenon of diffusion of a thermal disturbance produced by local warming of the part or sample. Investigation and characterization of the diffusion of the heat and of its variations at the surface of the part make it possible to detect or to characterize the part by detecting local variations in thermal diffusion.

Customarily, the device used or photothermal camera comprises a laser which is focused onto the surface of the part or sample under inspection, in a heating zone. The infrared flux radiated by the part in a detection zone neighboring the heating zone makes it possible to measure or evaluate the rise in temperature in the detection zone, due to the heating in the heating zone. The shift between the heating zone and the detection zone is generally referred to as the "offset". The flux radiated or the rise in temperature can be measured without contact by using a detector such as an infrared detector. The thermal flux radiated or the rise in temperature in the detection zone is influenced by the local characteristics of the materials examined. In particular, the diffusion of the heat between the heating zone and the detection zone which is the cause of the rise in temperature in the detection zone depends on the defects in the material, such as cracks, in the vicinity of the heating zone or of the detection zone or in the vicinity of both these zones.

In order to carry out non-destructive testing of the part made of the material or to carry out measurements of thermal diffusion in the material, a surface of the part or sample is scanned by displacing, at the surface of the part or sample, a means of imparting heat which generally consists of a laser beam focused onto a portion of the surface of the part constituting a heating zone.

The rise in temperature or the thermal flux radiated are determined in a detection zone whose position varies with the position of the heating zone, during the scan, the heating and detection zones being separated by a distance constituting the offset.

It is thus possible to obtain a two-dimensional image of the surface of the sample which is representative of the variations in diffusion of heat in the sample or else of the defects present inside the sample. Scanning can be achieved by using a fixed part and by displacing, over the surface of the part, the means for imparting heat synchronously with the detection zone; generally, scanning is carried out by deflecting a laser beam focused onto the surface, by using motorized steerable mirrors which are also used to send the flux radiated by the detection zone to a detector for measuring rise in temperature such as an infrared detector.

It is also possible to displace the part under examination past a fixed heating and detection device.

The scanning of the surface of the part is generally carried out by displacing, line by line over the surface, a pair of pointwise heating and detection zones, the heating and detection zones having for example circular shapes and small dimensions. As indicated above, a substantially point-like heating zone can be obtained by focusing a laser beam by means of spherical lenses onto the surface of the part or sample. Likewise, the infrared radiation emitted in a detection zone of small dimensions neighboring the heating zone is transmitted to an infrared monodetector in the form of a beam which is focused onto the sensitive surface of the detector which is generally of rectangular shape and of small dimensions.

The shift between the heating zone and the detection zone, referred to as the "offset" is altered by fine mechanical adjustment of the position of the infrared detector or of its focusing optics, in a plane parallel to the surface of the part under inspection.

Such a method or device using point-like heating and detection zones has certain drawbacks.

This method and this device may be fairly easily adapted to materials which are poor conductors from the thermal point of view and highly absorbent or emissive from an optical point of view. Specifically, the laser sources implemented in the case of active thermography have powers varying from a milliwatt to a few watts. These powers are insufficient in the case of materials which do not exhibit the abovementioned characteristics and in particular in the case of most metals.

Furthermore, these methods and devices have a low measurement productivity since it is necessary to perform a complete scan of the surface of the part or sample by displacing the point zones of heating and of detection.

The surface portion corresponding to the detection zone and the scanning rates to be implemented to obtain measurable signals are generally too small for the measurements performed to exhibit a genuine economical benefit, in particular in the case of the inspecting of metals and in the case of any material in which the diffusivity gradients which one wishes to determine are small, for example because they are due to small-sized defects.

The adjusting of the offset between the heating and detection zones which must be achieved by fine positioning and fine adjustment of the optical elements for heating and for detection or of the detector may be lengthy and tricky to implement. This adjustment must be reviewed periodically when it is desired to obtain good reproducibility of the inspection performance. In particular, it is in practice necessary to work at constant offset, thereby ruling out any possibility of optimizing the signal recorded and to work at zero offset if it is desired to carry out double scanning of the part so as to eliminate the effect of the surface condition of this part; the scan must also be limited to a single direction because the offset must be parallel to the direction of displacement of the heating zone and of the detection zone.

The inspection device can also have considerable proportions on account of the dimension of the laser source required, thereby ruling out the use of devices for testing parts on site, when the surfaces of these parts are difficult to access.

The optical heating and detection systems customarily used make it possible to obtain "field depths" of a few millimeters at best, these "field depths" consisting of intervals of variation of the distance between the inspection device and the surface of the part, in which intervals it is possible to obtain guaranteed performance of the inspection device. This low depth of field makes it impossible to examine parts which do not have strictly plane surfaces, this being the case for most of the parts to which thermographic testing may be applied.

It has been proposed, in the case of a thermographic inspection, to use several detectors operating in parallel, possibly in the form of an array (WO 8700632). However, this use of a set of detectors does not by itself make it possible to eliminate the drawbacks recalled above of the process for the thermographic inspection of a material.

The purpose of the invention is therefore to propose a method for the photothermal inspection of a material, consisting in carrying out the heating of a heating zone at the surface of a part made of the material, using a means of imparting heat, the detecting of a flux radiated by the surface of the part in a detection zone some distance from the heating zone, and the relative displacing of the heating zone and of the detection zone at the surface of the part along a defined scanning path, this method making it possible to avoid the drawbacks of the prior art methods which were described above.

For this purpose, the detecting of the flux radiated by the detection zone whose position varies with the position of the heating zone is carried out by selecting a group of detectors from among a set of detectors, the detectors of the group of detectors being arranged in such a way as to receive a flux radiated by the detection zone of the surface of the part, so as to optimize the photothermal inspection and to increase the speed of execution of this inspection.

To provide a better understanding of the invention, several embodiments of a method and of a device for photothermal inspection in accordance with the invention will now be described, by way of examples, in comparison with a method and a device for photothermal inspection according to the known art.

Figure 6A:
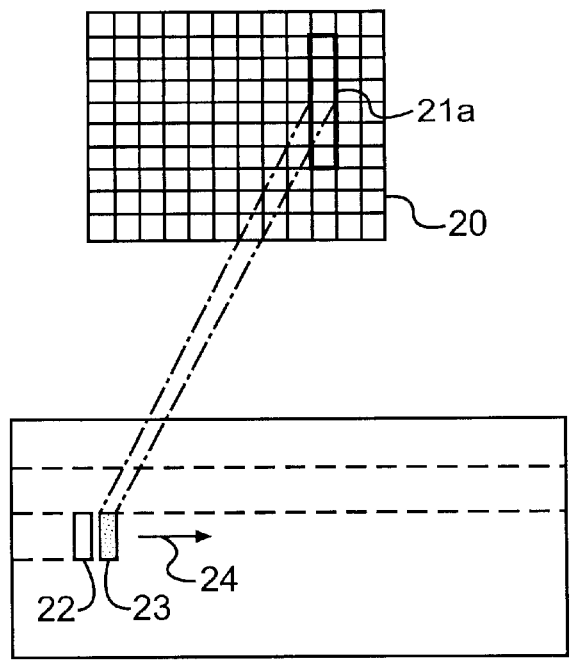
Figure 6B:
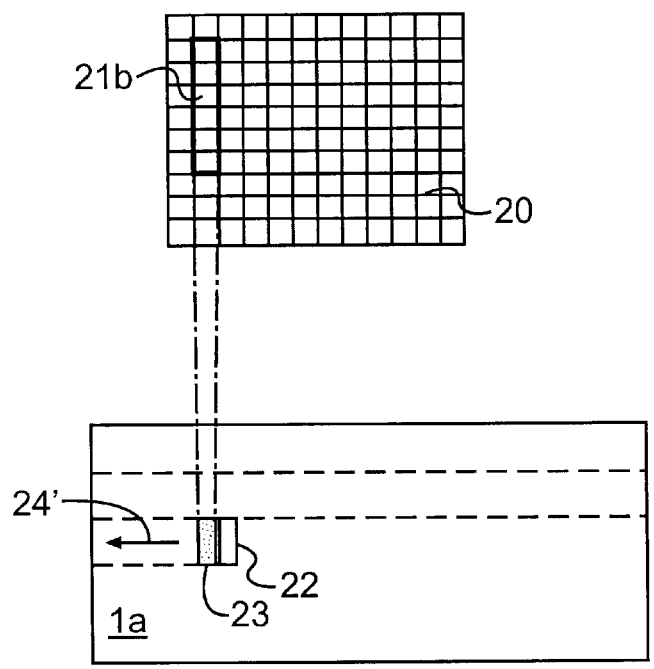
Figure 6C:
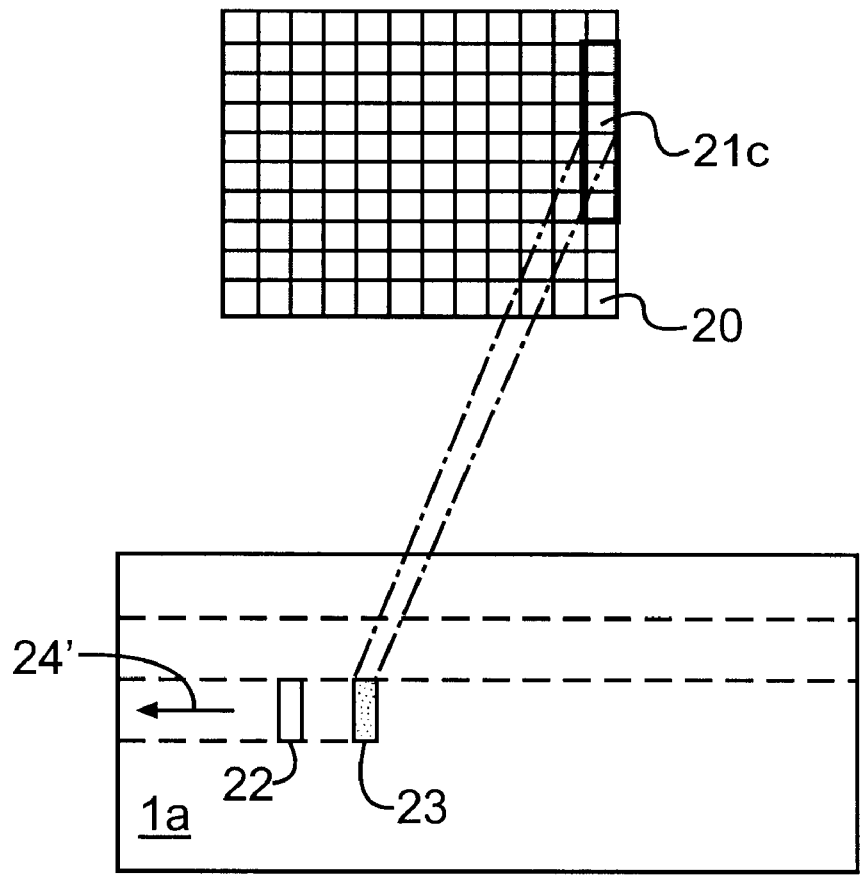

FIGS. 6A, 6B and 6C relate to the implementation of the method in accordance with the invention by scanning the surface of a part with adjustment of the offset between the heating and measurement zones as a function of the scan sense.

Figure 7A:
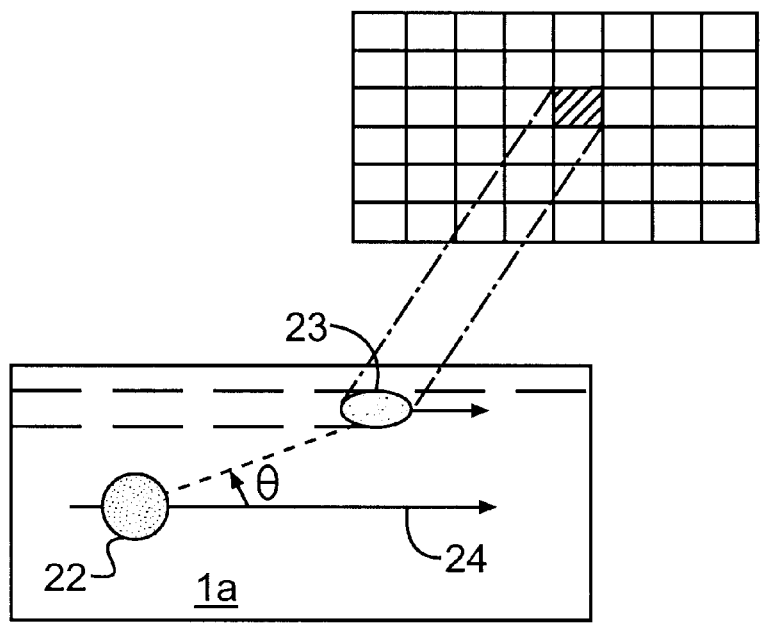
Figure 7B:
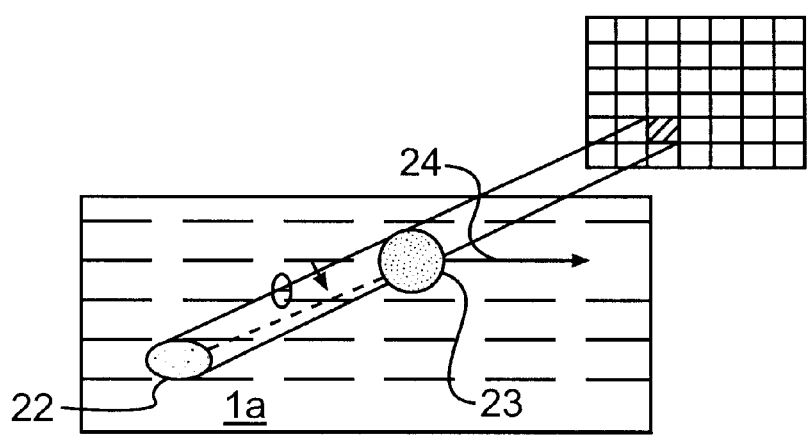

FIGS. 7A and 7B relate to the implementation of the method of the invention with an offset between pointwise heating and measurement zones having a different direction from the direction of scanning.

Figure 8:
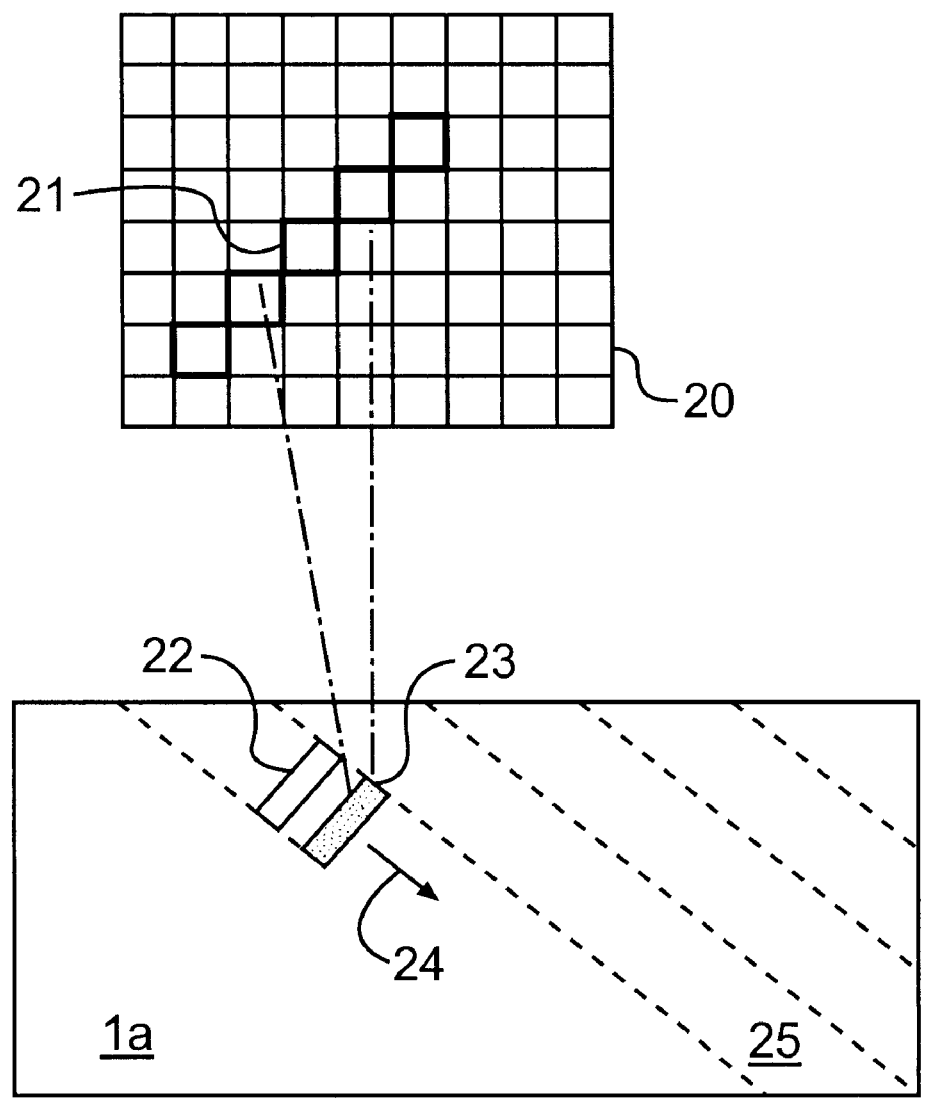

FIG. 8 relates to the implementation of the method of the invention with oblique scanning and the use of an oblique line of detectors of the matrix of detectors.

FIGS. 9A, 9B, 9C, 9D and 9E relate to the implementation of the method of the invention in point mode with adjustment of the offset between the point zones of heating and of detection, in direction, amplitude and sign.

Figure 10:
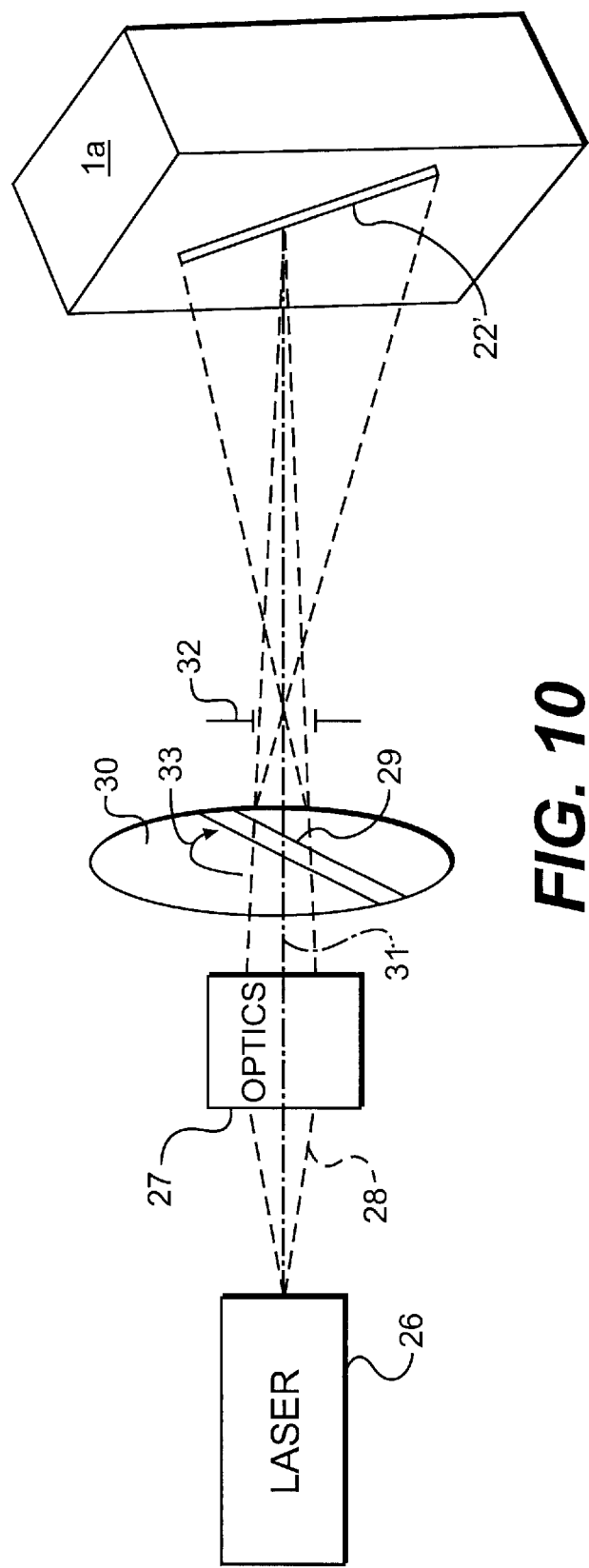

FIG. 10 is a view of a device in accordance with the invention making it possible to carry out a heating of the part to be inspected in a zone of elongate shape.

Figure 11:
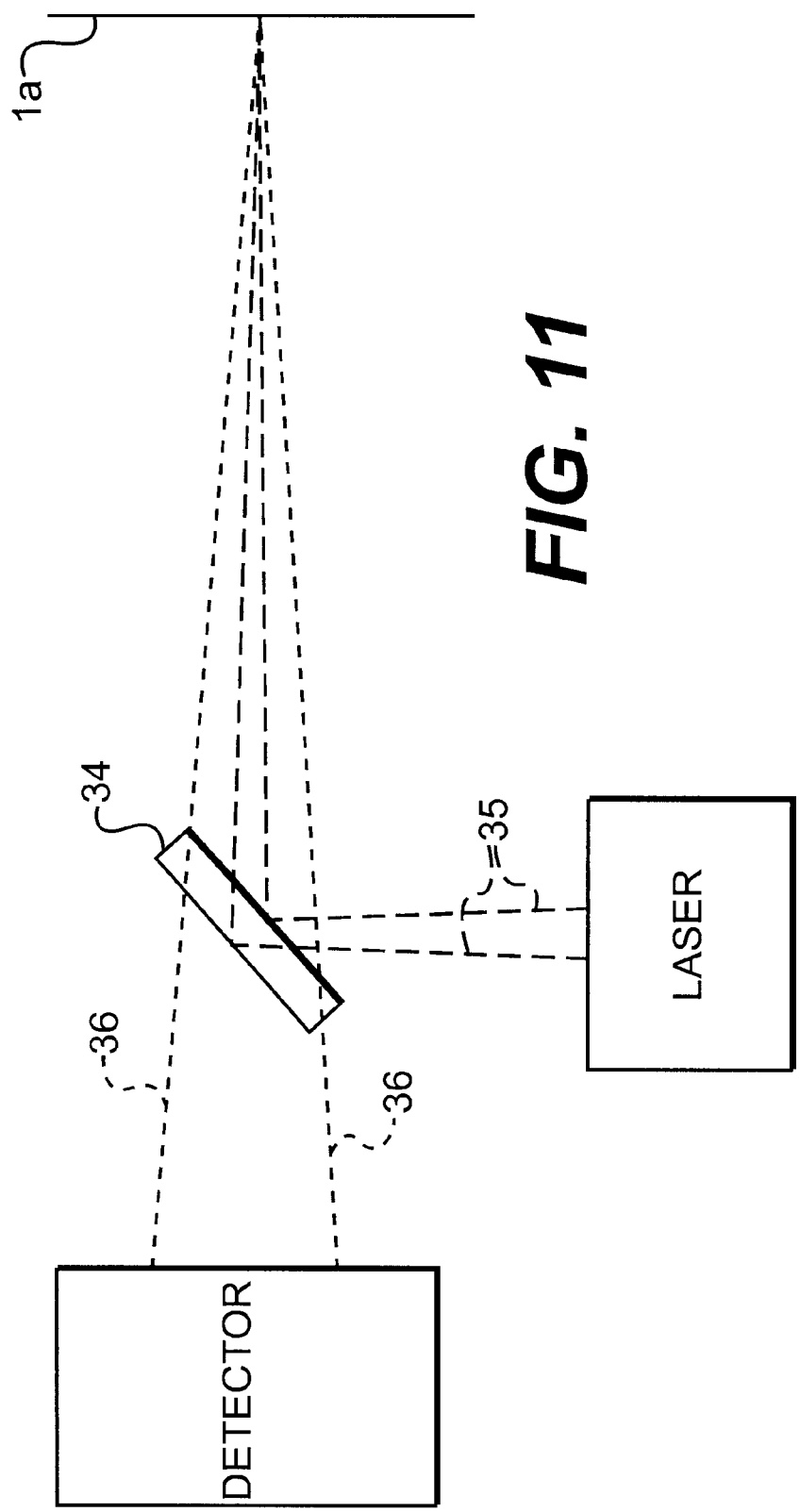

FIG. 11 depicts an optical setup for aligning the heating and detection fluxes in a device in accordance with the invention.

Figure 12:
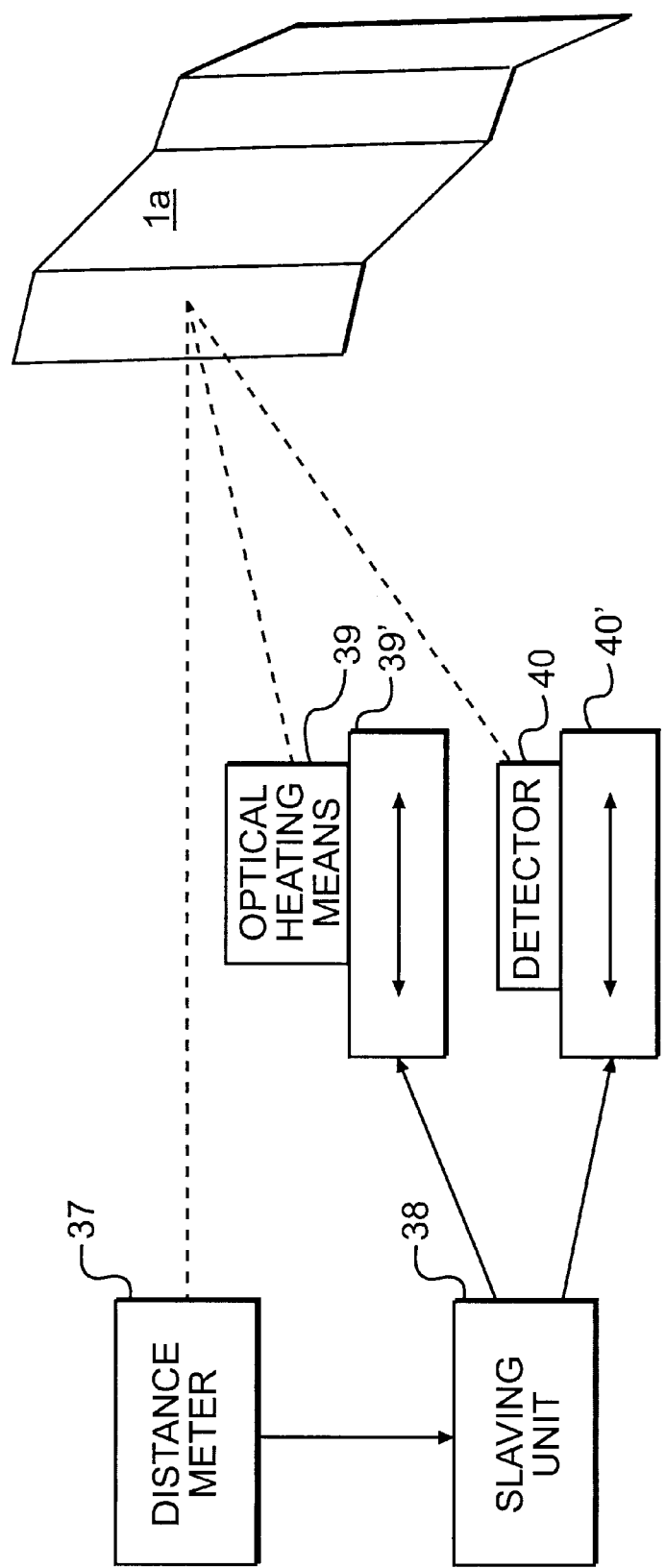

FIG. 12 is a schematic representation of a device making it possible to adjust the focusing of a beam for heating a part and the detected flux, during the scanning of the part.

Figure 13:
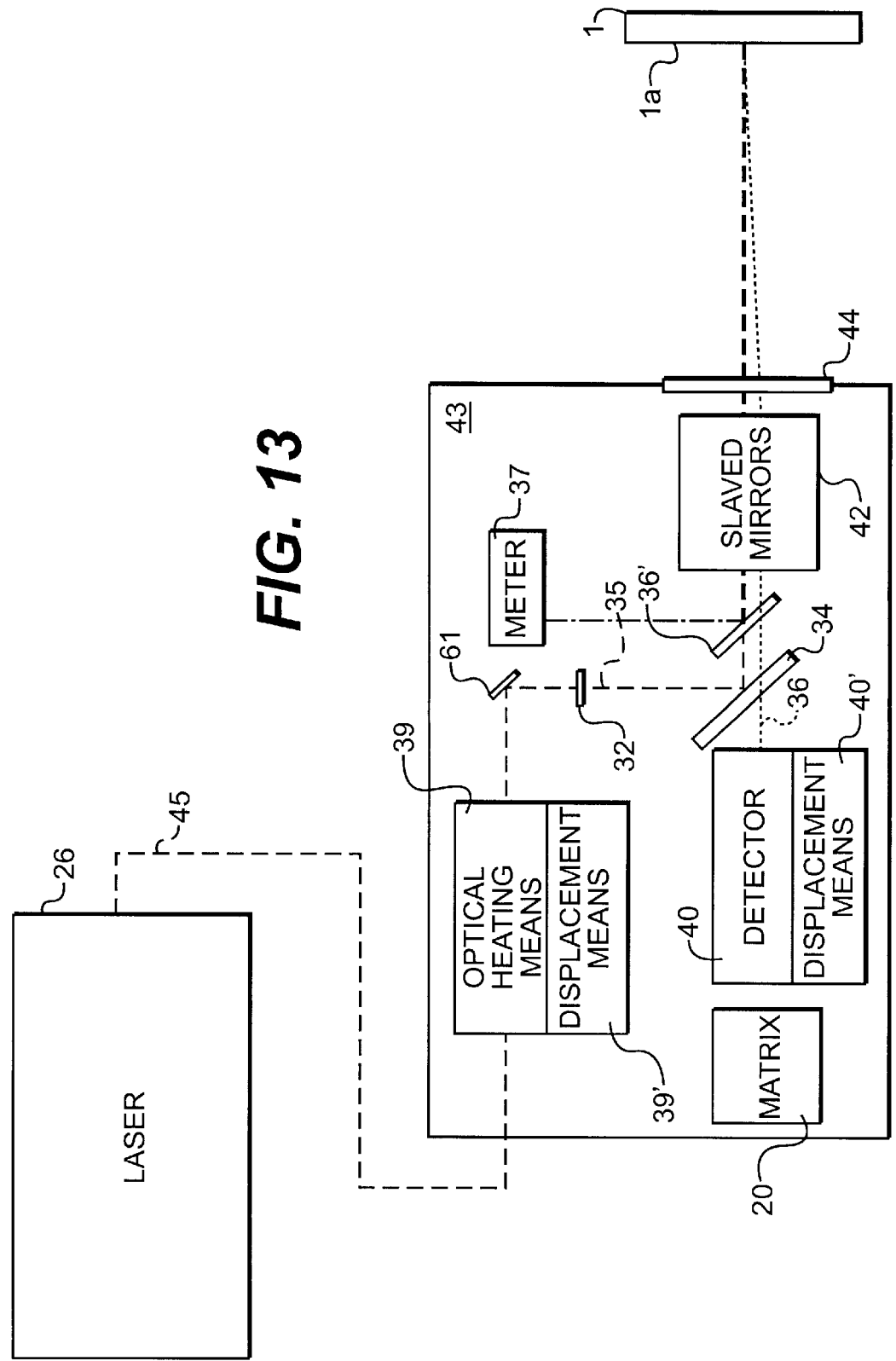

FIG. 13 is a schematic representation of an internal-scanning device for carrying out the testing of parts held in a fixed position.

Figure 14A:
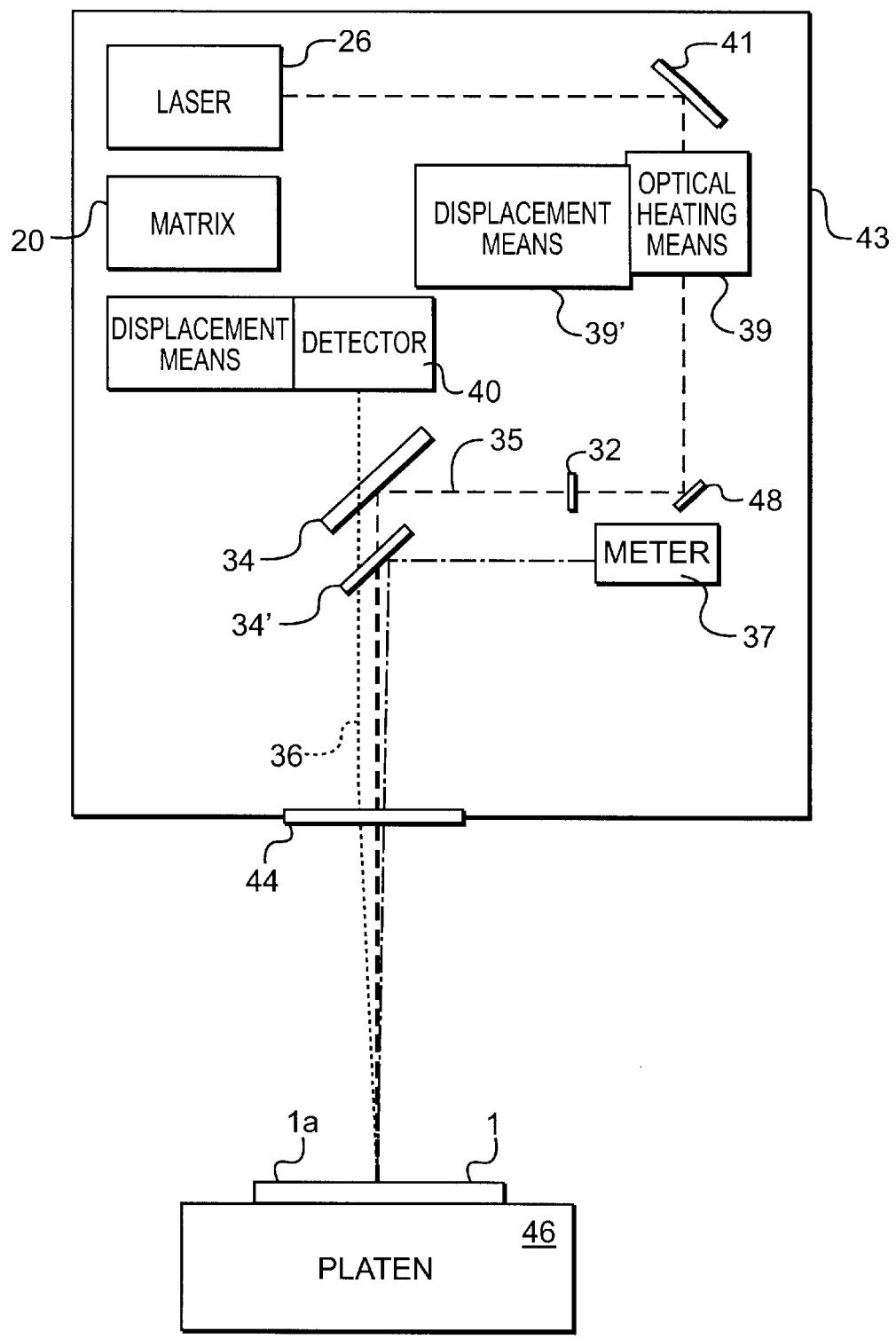
Figure 14B:
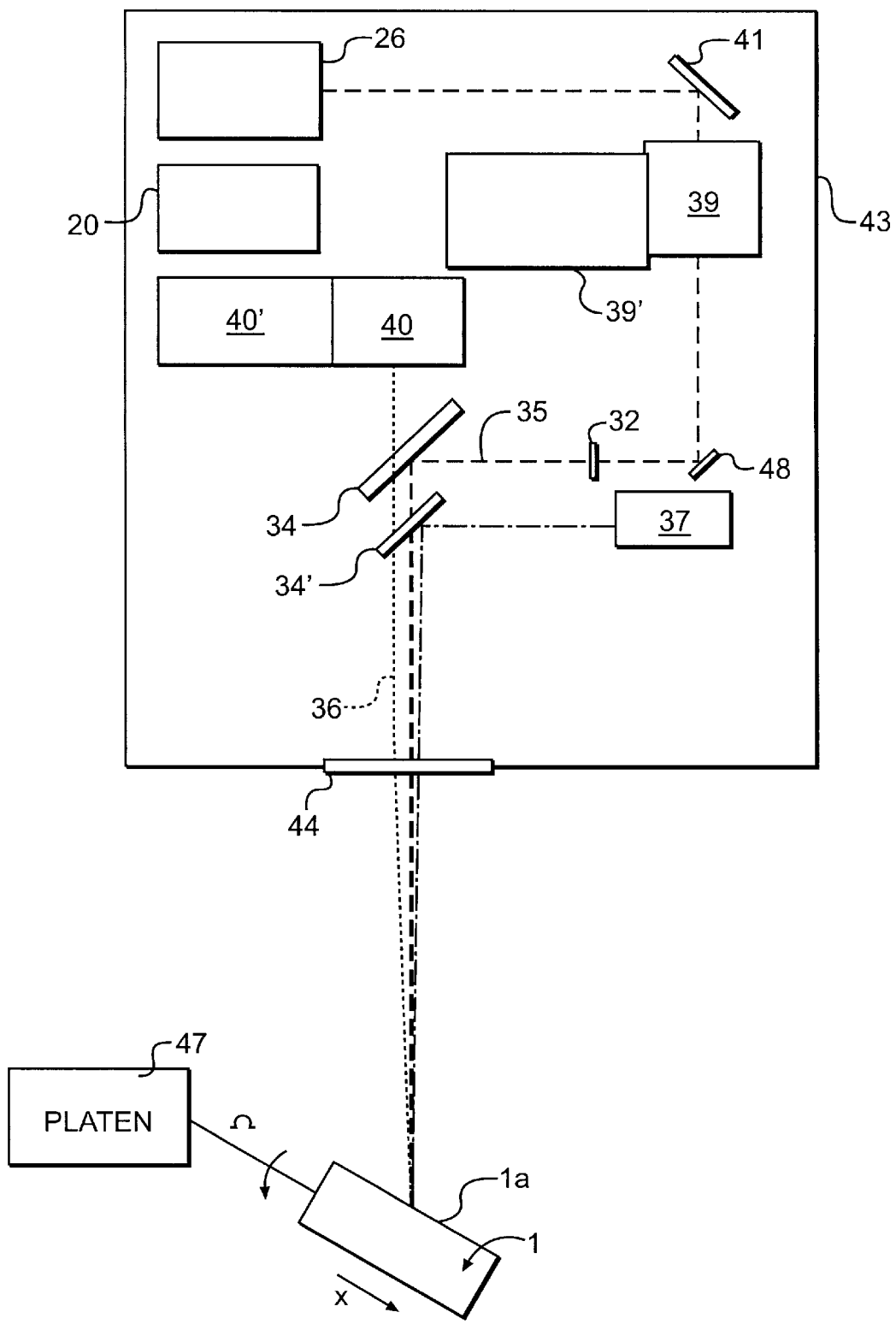

FIGS. 14A and 14B are schematic representations of devices in accordance with the invention in which the scanning is carried out by displacing the part to be inspected.

Figure 15:
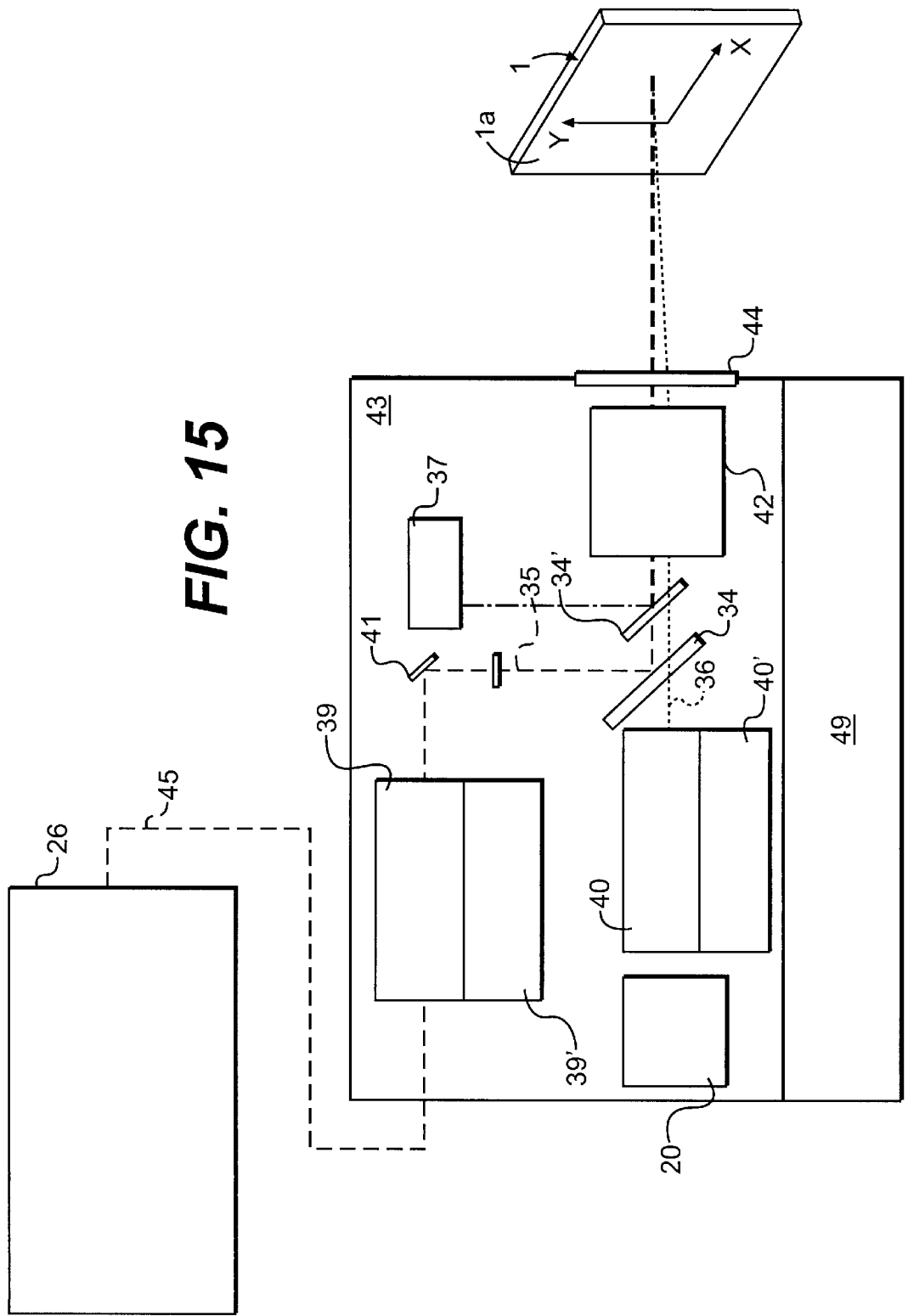

FIG. 15 is a schematic representation of a device in accordance with the invention with internal and external scanning for testing parts of any geometry.

Figure 16:
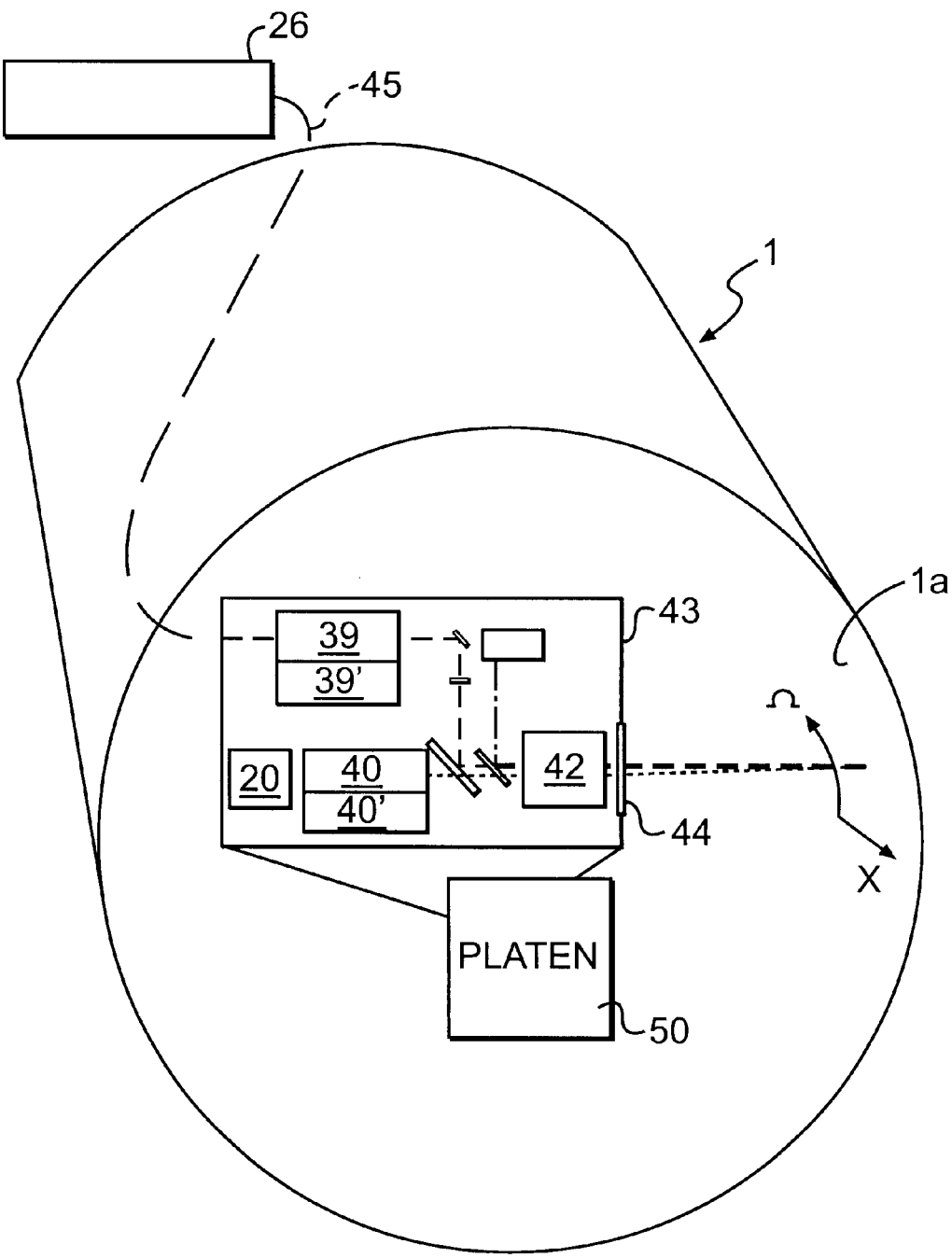

FIG. 16 is a schematic representation of a device in accordance with the invention with internal and external scanning for testing fixed parts of revolution.

Figure 17A:
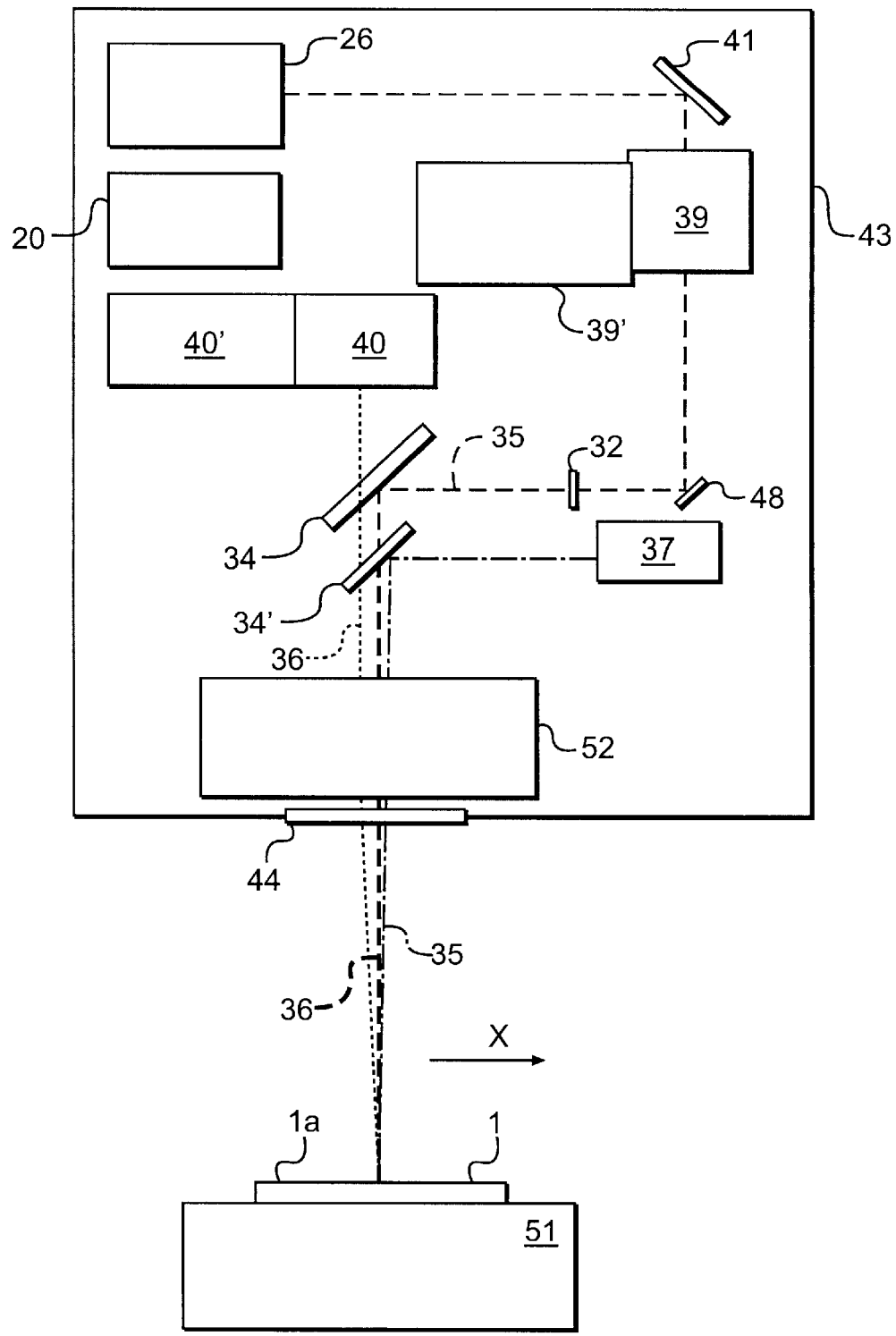
Figure 17B:
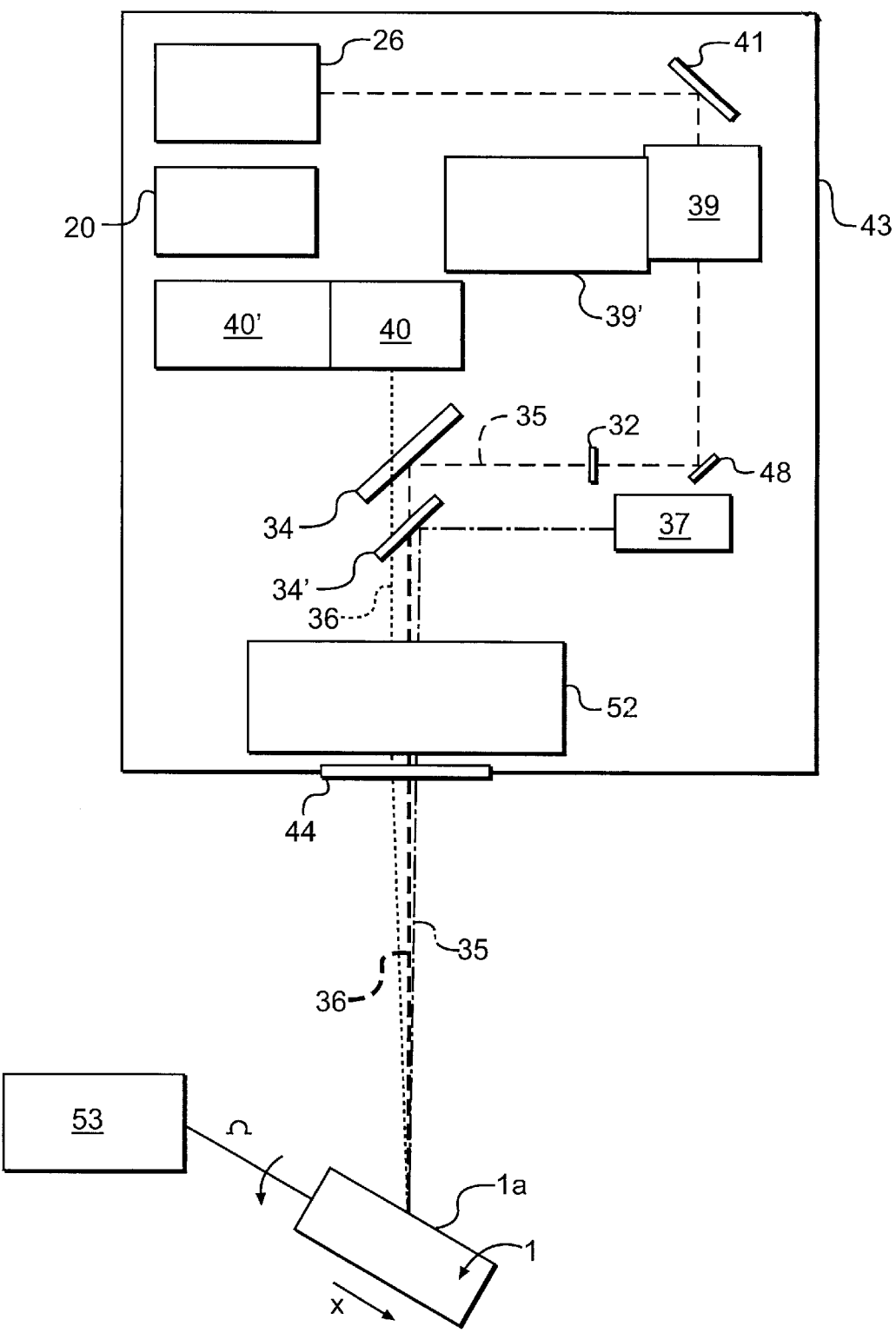

FIGS. 17A and 17B are schematic representations of devices in accordance with the invention with internal and external scanning equipped with means for displacing parts to be inspected.

Figure 18A:
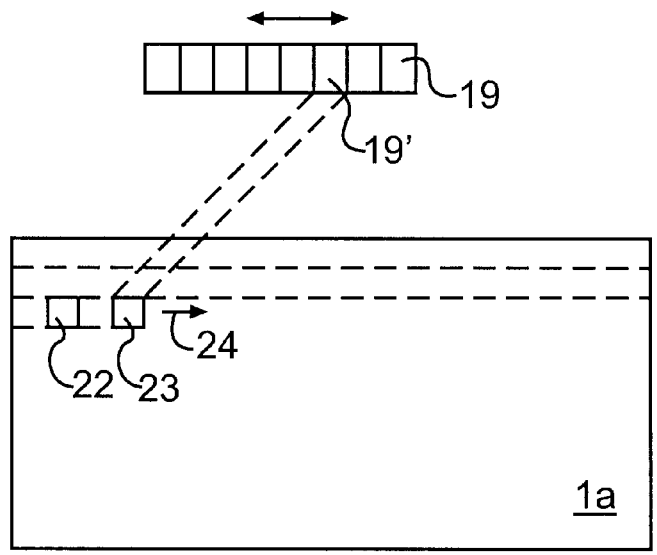
Figure 18B:
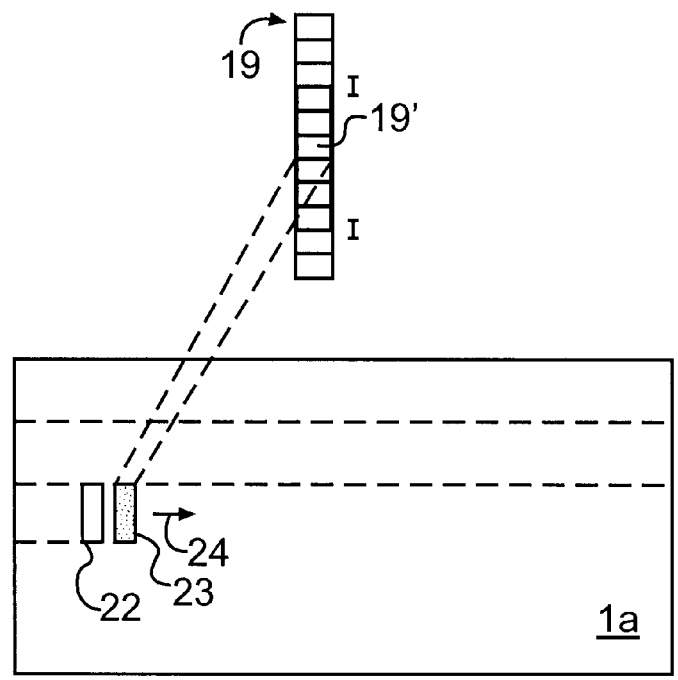

FIGS. 18A and 18B relate to the implementation of the method in accordance with the invention with a single strip of detectors.

Figure 1:
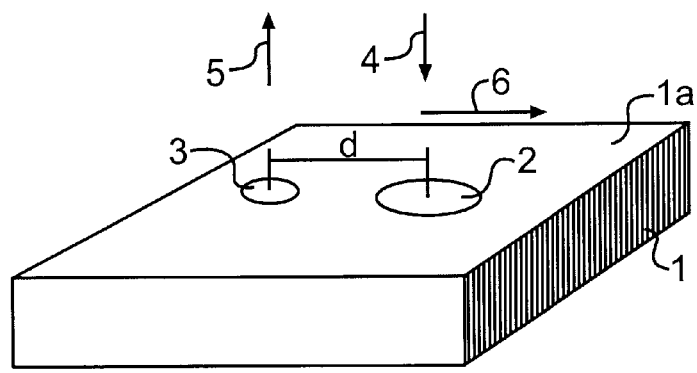
FIG. 1 is a schematic perspective view of a part made of a material on which a photothermal inspection is performed.

Represented in FIG. 1 is a part 1 consisting of a material whose photothermal inspection is to be carried out, the general shape of which is right-angled parallelepipedal and which includes a plane surface 1a on which is carried out the heating of the material of the part 1 in a zone 2 of the surface 1a by imparting heat, for example in the form of a laser beam, as represented schematically by the arrow 4. By using a detector, the flux radiated by a detection zone 3 of the surface 1a, as represented schematically by the arrow 5, is detected. The heating zone 2 and the detection zone 3 are offset with respect to one another on the surface 1a and separated by a distance d referred to as the offset.

To carry out the inspection of the part 1, the surface 1a is scanned by displacing the heating zone 2 and the detection zone 3 in a synchronous manner, over the surface 1a, as indicated by the arrow 6 parallel or otherwise to the offset between the heating zone and the detection zone. The scanning is carried out line by line, the sense of the displacement being reversed for each of the successive lines ("notch" configuration) or identical ("comb" configuration).

Figure 2:
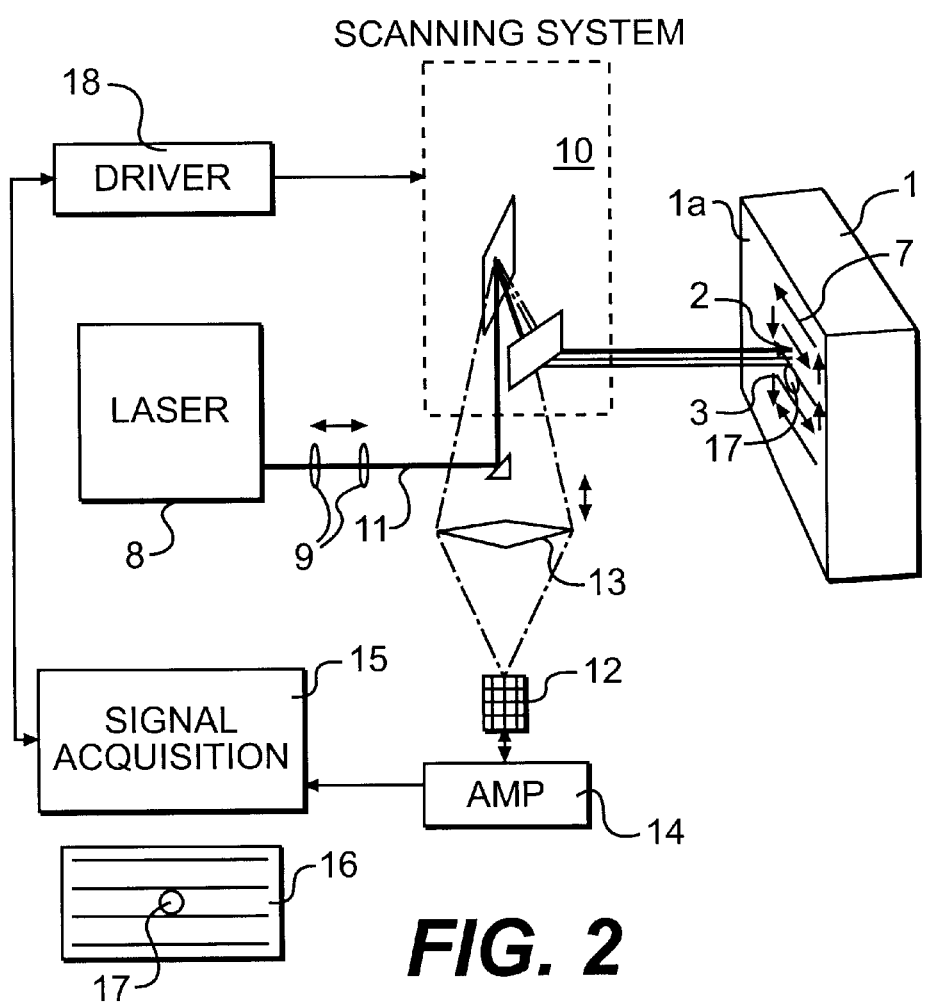
FIG. 2 is a schematic representation of an inspection device such as a photothermal camera.

Represented schematically in FIG. 2 is a device for the photothermal inspection of the part 1, with scanning of the surface 1a of the part along successive scan lines, as represented by way of example in the "notch" configuration by the arrows 7, on the face 1a of the part 1.

The device includes a laser source 8 associated with focusing lenses 9 and with a scanning system 10 which consists of motorized pivoting mirrors.

The focusing lenses 9 make it possible to focus the laser beam 11 originating from the laser source 8 onto the surface 1a of the part 1, in the vicinity of the heating zone 2. The scanning system 10, consisting of the motorized pivoting mirrors, makes it possible to displace the heating zone 2 along the scanning path 7 over the surface 1a of the part 1. Moreover, the scanning system makes it possible to convey, at each instant, to an infrared monodetector 12, by way of an infrared optical collecting and focusing system 13, the infrared radiation emitted by a detection zone 3, which can be slightly offset with respect to the heating zone 2.

On output from the infrared monodetector 12, the signals produced by the monodetector and which are representative of the infrared radiation emitted by the detection zone are amplified by an amplifier 14 and then transmitted to a unit 15 for acquiring and synchronizing the signals and for constructing an image representing the variations in the local thermal properties of the surface 1a.

The image formulated by the unit 15 is displayed on a screen 16. In the case of the presence of a defect 17 or of a variation in thermal properties within the material of the part 1, the defect 17 is made visible at 17' on the screen 16 of the photothermal device or photothermal camera.

The unit 15 is linked to a unit 18 for driving the scanning system 10 in such a way as to carry out the synchronization of the scanning system with the signal acquisition system.

Figure 3:
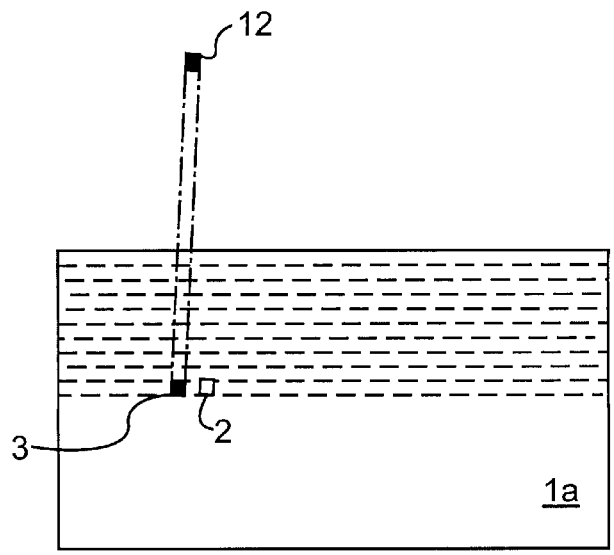
FIG. 3 is a schematic showing the implementation of a method of photothermal inspection according to the prior art with scanning of a surface of a part by pointwise zones.

Represented schematically in FIG. 3 is the surface 1a of the part on which a scan is carried out by displacing a point zone of heating 2 corresponding to the zone of focusing of a laser beam and of a point detection zone 3 whose infrared radiation is detected by the monodetector 12.

As may be seen in FIG. 3, a line-by-line scan is carried out in such a way as to cover the entire surface 1a of the part in the course of the scan. For each of the positions of the heating 2 and detection 3 zones, the acquisition of a pixel of the photothermal image of the surface 1a is carried out. As indicated earlier, in this case which corresponds to the arrangements according to the prior art, a very low productivity of measurement is obtained since it is necessary to perform a complete scan of the surface 1a of the part to be examined and since the rates of scan for obtaining acceptable signals on output from the monodetector 12 may be limited.

Furthermore, the offset, that is to say the shift between the zones 2 and 3 must be adjusted accurately before beginning the inspection of the surface 1a by fine mechanical adjustment of the position of the detector 12 or of the optical system 13 in a plane parallel to the surface 1a. The offset between the zones 2 and 3 cannot be adjusted in the course of inspection and adapted to obtain signals which are as characteristic as possible of the variations in the thermal properties which one seeks to record.

Figure 4:
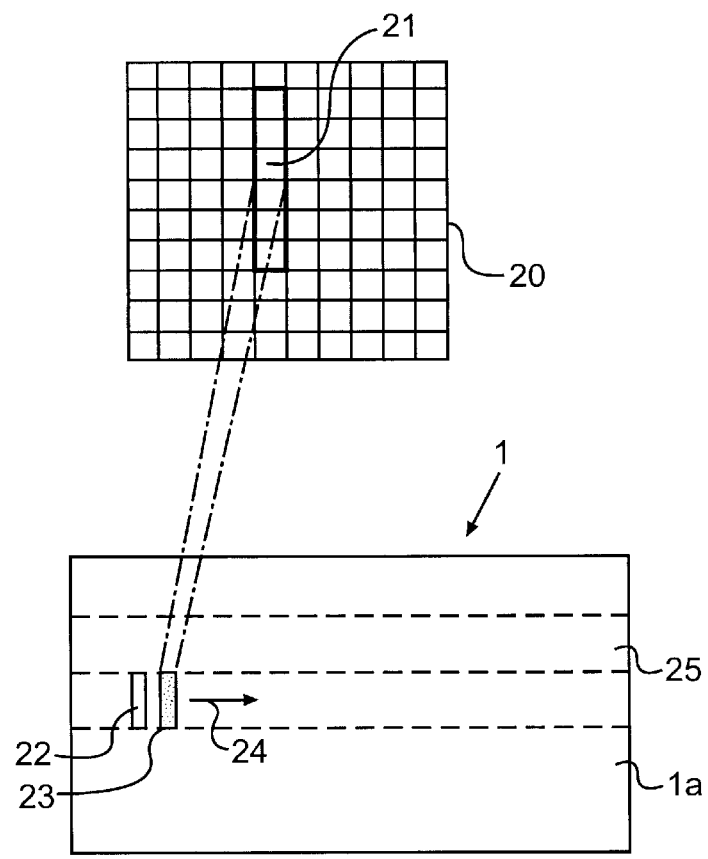
FIG. 4 is a schematic view similar to the view of FIG. 3 relating to the implementation of the method of photothermal inspection in accordance with the invention.

Represented schematically in FIG. 4 is an exemplary implementation of a method in accordance with the invention.

The method in accordance with the invention is implemented in order to carry out the thermographic inspection of a surface 1a of a part made of a material on which a non-destructive test or a measurement of thermal properties is performed.

Unlike the exemplary implementation of a method of thermographic inspection according to the prior art represented in FIG. 3, use is made, in order to carry out the detection of a radiation emitted by a detection zone of the surface 1a, rather than of a monodetector such as the monodetector 12 represented in FIG. 3, of a matrix of detectors 20, that is to say a set of unit infrared detectors whose sensitive surface has the shape of a square or a rectangle of small dimensions, arranged as an orthogonal-mesh array having N columns and M rows.

The number of columns N and the number of rows M of the matrix 20 may lie between 1 and several hundred (for example 512). The numbers may be fixed independently of one another.

The method in accordance with the invention consists, as in the case of the methods according to the prior art, in displacing, over the surface 1a of the part under inspection, a heating zone 22 and a detection zone 23, in such a way as to scan the whole of the surface 1a and to capture and measure the radiation emitted by the detection zone 23 with the aid of infrared detectors.

It is known practice, as indicated earlier, to carry out the detection by using a monodetector and pointwise heating and detection zones. It is also known practice to use a complete matrix of detectors to observe the temperature trend over the complete surface of a part subjected to a source of heat.

As compared with these known methods, the method of the invention carries out a scan of the surface 1a of the part in heating 22 and detection 23 zones and the detection of the radiation emitted by the detection zone 23 moving at the surface of the part 1a by a group of juxtaposed detectors 21 of the matrix of detectors 20.

In the case of the embodiment represented in FIG. 4, the group 21 of juxtaposed detectors of the matrix of detectors 20 constitutes a part of a column of this matrix of detectors 20 comprising n juxtaposed detectors. As will be explained later, the position of the column of detectors is carefully chosen within the matrix 20 so as to carry out detection under ideal conditions.

The set of detectors chosen can be arranged either column-wise, row-wise or along a diagonal of any slope.

The signals of each of the detectors which have been chosen can be processed independently.

Owing to the use of a set of detectors, it is possible to use elongate heating 22 and the detection 23 zones rather than point zones. These elongate zones 22 and 23 cover a certain length of the surface of the sample 1a which corresponds to the image delivered through exploitation of the signals of the detectors, in the form of n pixels.

The scanning of the surface 1a in elongate zones 22 and 23, as shown schematically by the arrow 24, makes it possible to cover, at each of the displacements in the sense of the arrow 24 along the length of the surface 1a, a band 25 of the surface whose width corresponds to n pixels of the image. It is thus possible to carry out a complete scan of the surface 1a of the part in successive bands 25 whose area may be several hundred times larger than the area of a scan line when using a point zone 2, 3 and a monodetector 12.

The length of the group 21 of detectors of the matrix 20 catering for the detection of the radiation emitted by the detection zone 23 is chosen as a function of the characteristics of the part under inspection. A considerable length of the line of detectors 21 will be chosen, in the case of a part with large dimensions and a more reduced length in the case of a part with small dimensions or a complicated geometry.

Figure 5A:
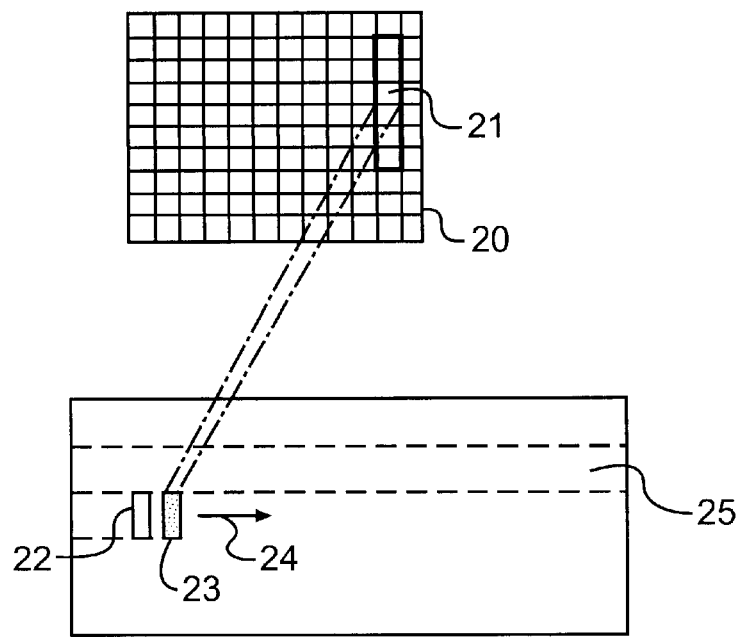
FIGS. 5A and 5B are schematic views relating to the implementation of the method of the invention, with adjustment of the offset between the heating and detection zones.
Figure 5B:
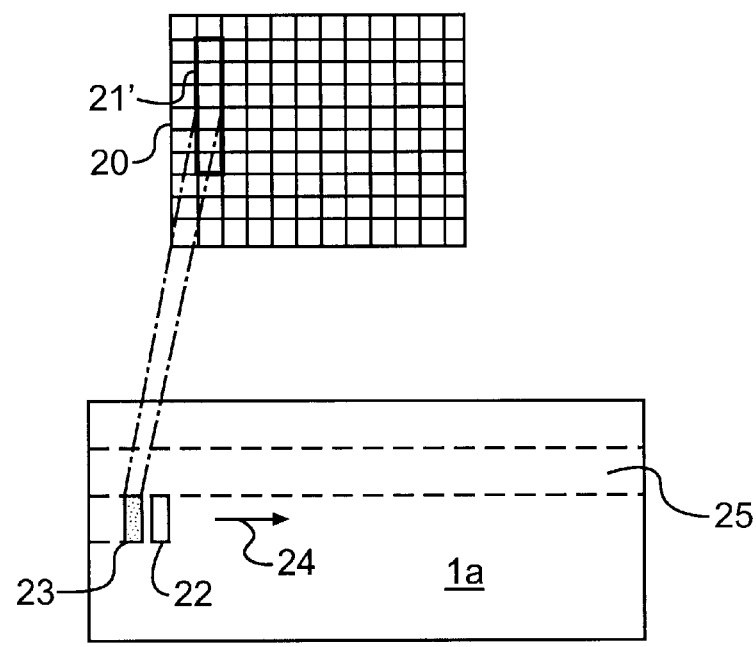

Represented schematically in FIGS. 5A and 5B are two variants of the use of the method in accordance with the invention, in such a way as to adjust the offset between the heating zone 22 and the detection zone 23, that is to say the distance separating these two zones in the direction of the scan line or band 25, without having to perform any mechanical adjustment of the means of imparting heat, of the means of detection, or of their optics.

In FIG. 5A, to carry out the detection of the radiation emitted by the zone 23, use is made of a first column of detectors 21 of the matrix of detectors 20, so that the offset between the zones 22 and 23 has a first positive value, taking the sense of the arrow 24 as the positive sense.

In FIG. 5B it has been shown that by using a second column of detectors 21' distinct from the column 21 in the matrix of detectors 20, the offset between the zones 22 and 23 is fixed at a different and negative value by taking the sense of the arrow 24 as the positive sense.

By a simple electronic or "software" adjustment of the detection device, it is therefore possible to instantaneously optimize the adjustment of the offset in such a way as to obtain the best possible signal/noise ratio, during the adjustments performed before examining a part or a series of parts.

As may be seen in FIGS. 6A, 6B and 6C, it is also possible to implement a method of double scanning of the surface 1a, that is to say a method in which the scanning of each of the bands 25 is carried out in succession in a first sense (the sense of the arrow 24) and in a second opposite sense (the sense of the arrow 24').

Such a double-scanning method, which forms the subject of a patent application filed on the same day as the present patent application, makes it possible, by pointwise subtraction of the signals or of the images obtained by thermography for the first and the second scan senses, respectively, to eliminate the variations in emissivity or in absorptivity of the surface 1a which are liable to mask the variations in the thermal diffusion in the material of the part, on which variations the inspection or photothermal testing of the part relies.

In FIG. 6A it may be seen that the choice of a first column of detectors 21a of the matrix of detectors 20 makes it possible to fix the offset between the zones 22 and 23 at a first value, while displacing the zones 22 and 23 in the sense of the arrow 24 or outward sense of the scan.

As may be seen in FIG. 6B, it is possible, while displacing the zones 22 and 23 in the second displacement sense given by the arrow 24', corresponding to the return sense of the scan, to fix the offset at a value which is identical in amplitude and in sign to the value during the displacement in the outward sense, by choosing a second column of detectors 21b from the matrix of detectors 20. The aim of such a modification of the offset between the outward and return legs is to fully eliminate the improper information or to increase the signal/noise ratio of the examination.

As may be seen in FIG. 6C, during the displacement in the return sense 24', it is possible to modify both the amplitude and the sign of the offset between the outward and the return, by choosing a third column of detectors 21c of the matrix of detectors 20.

As may be seen in FIGS. 7A and 7B, it is possible, using the method of the invention, by choosing a particular detector of the matrix of detectors, to carry out the inspection of the surface 1a of the part in point mode, that is to say in such a way that the detection zone 23 corresponds to a single pixel of the thermographic image obtained by scanning the surface. One pixel corresponds to an element of the matrix.

The use of a matrix of detectors and the choice of a particular detector from the matrix of detectors makes it possible to carry out, as may be seen in FIGS. 7A and 7B, the scan in the direction 24 with a detection zone 23 sited in such a way that the offset between the zones 22 and 23 lies in a direction making an angle θ with the direction of scan 24. This embodiment of the thermographic inspection which is not possible in the case of the use of a monodetector makes it possible to improve the thermographic image when the surface 1a of the part exhibits a surface condition which makes the double-scan testing process less effective.

As may be seen in FIG. 8, it is possible to modify the direction of the scanning axis 24 and hence the direction of the bands 25 on the surface of the part 1a and to choose a group of detectors 21 of the matrix of detectors 20, which group consists of detectors defining rectilinear rows arranged in any manner whatsoever on the matrix of detectors. The direction of the scan can be fixed or modified at any instant so as to be established in any direction of the surface 1a. Adjustment of the orientation of the direction of scan can thus be performed with a latitude of 360°.

This adjustment or this modification of the direction of scan can be carried out equally well in the case of operation in line mode, that is to say with elongate heating and detection zones 22 and 23 and using a line of detectors, as in point mode, that is to say with heating and detection zones corresponding to a single pixel of the thermographic image.

Represented in FIGS. 9A to 9E are various possibilities for adjusting the direction of scan 24 of the surface of the part and of the offset between the heating 22 and detection 23 zones, in the case of operation in point mode.

Figure 9A:
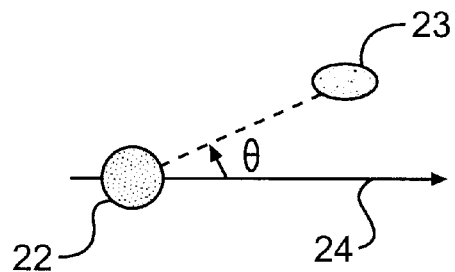
Figure 9B:
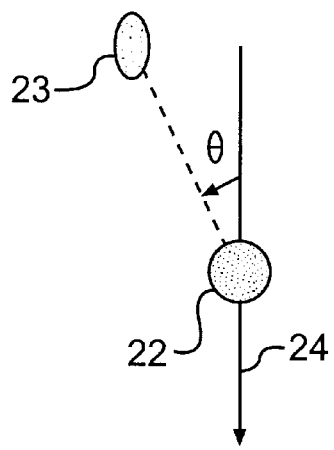

As may be seen in FIGS. 9A and 9B, the point zones 22 and 23 may be aligned along a direction making an angle θ with the direction of scan. In this case, the offset can be adjusted in direction and in amplitude.

Figure 9C:
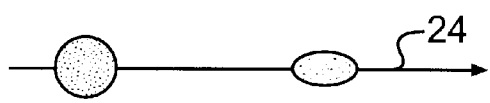
Figure 9D:
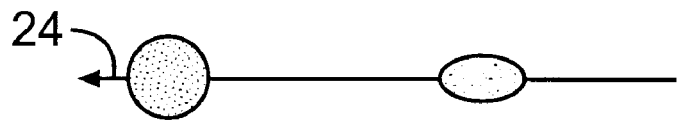

As may be seen in FIGS. 9C and 9D the offset can be directed in the scanning sense given by the arrow 24 or in the reverse sense.

Figure 9E:
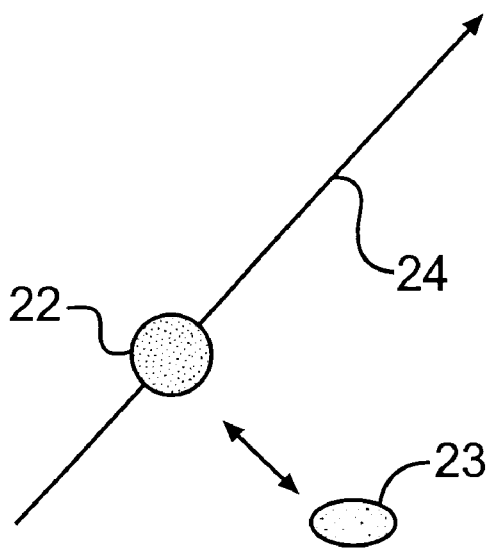

As may be seen in FIG. 9E, the point zones 22 and 23 may be aligned along a direction which is almost perpendicular to the direction of scan 24.

In all cases, the offset can also be adjusted in amplitude in addition to the adjustment in direction.

Owing to the use of a matrix of detectors and to the scanning of a surface of the part to be inspected, the method in accordance with the invention therefore makes it possible to employ numerous means for improving the signal/noise ratio, whether the inspection be carried out in line mode or in point mode, by single scanning or by double scanning. These means are in particular the adjusting of the offset between the heating and detection zones, in terms of sign, value and angular direction.

As indicated earlier, the method in accordance with the invention also makes it possible to carry out the inspection by implementing a different distribution of the intensity of the heating laser from that of a zone of circular Gaussian type. The method and the device in accordance with the invention implementing a matrix of detectors and scanning of the surface makes it possible to implement a heating zone of linear type having for example the shape of a line or of an ellipse. It is also possible to implement a heating zone of annular shape.

Represented schematically in FIG. 10 is a device making it possible to carry out a scan of the surface 1a of the part or sample with a heating zone 22' having the shape of an elongate ellipse.

The device includes a laser source 26, optical means 27 of focusing the laser beam 28, optical means of forming a linear zone 29 receiving laser radiation, on a support 30 which can be oriented by 180° about the optical axis 31 of the device and an aperture-adjustment diaphragm 32.

The optical means 27 of focusing and of forming the line 29 on the support 30 may be mounted on distinct supports and, in this case, the support of the optical means of focusing 27 is held fixed whilst the support of the means of forming the line 29 is mounted rotatably, as indicated by the arrow 33. They may also be mounted on a common support which is then mounted rotatably about the optical axis 31.

The linear heating zone 22' may thus be oriented in any direction about the axis 31, this direction being chosen as a function of the direction of scanning of the surface 1a.

It is also possible, by virtue of the diaphragm 32, to adjust the length of the heating zone 22', from the zero value up to a maximum value determined by this maximum aperture of the diaphragm 32.

By adjusting the length of the heating zone 22' to a value substantially equal to the width of this heating line, it is possible to carry out an inspection in point mode. To increase the power density of heating, in the case of operation in point mode, it is possible to omit the optical means of forming the line 29. Of course, the means of adjusting the orientation of the line 29 and of adjusting the aperture of the diaphragm may be motorized.

Represented in FIG. 11 is an optical setup making it possible to transmit the heating beam 35 and to recover the detection beam 36 on the surface of the sample 1a, with very good efficiency and in such a way that the beams are colinear over that part of their optical journey which intercepts the part to be examined.

The device includes a semi-reflecting plate or dichroic plate 34 which is interposed in the path of the heating beam 35 originating from a laser source, in such a way as to divert this beam onto the surface 1a of the part to be inspected, with a high coefficient of reflection. The dichroic plate 34 also makes it possible to transmit, with a high coefficient of transmission, the infrared flux 36 or detection beam emitted by the surface of the sample 1a, the beams 35 and 36 having a common optical path length between the surface 1a of the part or sample and the dichroic plate 34.

The dichroic plate could also transmit the laser ray and reflect the detection flux IR. In this case, the arrangement of the laser and the arrangement of the detector are reversed.

When the part 1 has a complex shape, the surface 1a of this part on which the scan is carried out can exhibit successive zones whose distance to the optical means of heating and detection can vary considerably. In this case, during scanning, it is necessary to vary the adjustment or the position of the heating and detection devices.

Represented in FIG. 12 is a device which includes means of slaving the position of the optical means of heating or of excitation 39 and of the optical means of detection 40 of the distance between the zone of the surface 1a in which the scan is carried out and these optical means. The distance measurement is carried out by a meter 37 which can be a telemeter, an interferometer or a triangulation-based distance sensor. The optical axis of the distance meter 37 is rendered colinear with the optical axis of the excitation optic 39 and with the optical axis of the detection means 40.

The information relating to the distance measured by the distance meter 37 is transmitted to electronic slaving means 38 controlling a platen 39' for displacing the optical means of excitation 39 and a platen 40' for displacing the infrared detection means 40.

The slaving of the focusing of the optical means of heating 39 and of the means of detection 40 can be carried out in real time, that is to say that for each of the positions of the heating and measurement zones, a distance measurement is performed by the distance meter 37, which is transcribed into a positioning command for effecting the displacement in real time of the means of heating 39 and of detection 40 by the corresponding displacement platens 39' and 40'. This slaving can also be performed in non-real time, a topology of the surface 1a of the part being recorded during a first scan implementing only the distance meter 37. The information obtained during the first scan is stored in memory and used by the platens 39' and 40' during a second scan in the course of which the thermographic inspection is carried out.

In the case of real-time slaving of focusing, the alignment of the beam of the distance meter on the optical axes of the heating 39 and detection 40 means is effected by way of a dichroic plate installed permanently on the transit of the beams. In the case where the measurement is carried out in non-real time, alignment is carried out by a simple mirror which is sited in the track of the measurement beam during the first scan allowing topographical charting of the surface 1a, this mirror thereafter being removed during the thermographic measurement.

The positional slaving of the optical means of heating and detection can also be carried out on the basis of a theoretical information item concerning the shape of the surface 1a of the part, for example in the form of CAD data.

The main benefit of the method and the device in accordance with the invention which were described above is that they make it possible to carry out the inspection of materials of entirely diverse natures and in particular exhibiting very different thermal properties. The inspection method and device in accordance with the invention also apply to parts exhibiting any surface conditions whatsoever and hence absorptivity and emissivity properties which exhibit large variations over the surfaces under inspection.

In the implementation of the method in accordance with the invention in point mode, the heating zones can have a substantially square or rectangular shape or else circular or annular shapes. In this case, the side of the square or the diameter of the circular zone has a length L which may lie between 20 $\mu$m and 10 mm.

The offset between the heating zone and the detection zone can go from −5L to +5L in a direction defined by an angle of 0 to 360° with respect to the direction of scan. The rate of displacement of the heating and detection zones during scanning may be between 0.1 and 100 mm/s. The length of the scan line may be between L and 50 mm. The power density imparted to the material examined may be of the order of 0.1 to 200 W/mm$^2$, as a function of the optical absorptivity and the thermal diffusivity of the material and of the rate of scanning.

Represented by way of examples in FIGS. 13, 14A, 14B, 15, 16, 17A and 17B are various embodiments of a device making it possible to implement the method in accordance with the invention.

The corresponding elements in all the figures bear the same labels.

In general, the devices include the following elements:
a source of laser radiation 26,
optical means of heating 39 associated with the laser source and means 39' of displacing these heating means 39,
a matrix of detectors 20, infrared optical means of detection 40 and means 40' for displacing these infrared optical means,
a distance meter 37,
a dichroic plate 34 and a retractable mirror 34',
a diaphragm 32,
a mirror 41 for diverting the heating beam.

The heating beam is designated by the label 35 and the detection beam by the label 36.

The hood 43 furnished with a transparent exit port 44 makes it possible to protect part at least of the optical device.

In the case of FIG. 13, the source of laser radiation 26 is arranged outside the hood 43 and linked to the optical heating means 39 by way of an optical fiber 45.

The scanning of the surface 1a of the sample 1 in two perpendicular directions X and Y is carried out by a set of pivoting mirrors 42 driven by control electronics.

In the case of the devices represented in FIGS. 14A and 14B, the scanning of the surface 1a of the sample 1 is carried out by a platen 46 or 47 for displacing the sample, the whole of the optical device sited inside the hood 43 being totally fixed and sending a heating beam 35 to the surface 1a of the sample and gathering a detection beam 36 of fixed direction.

In the case of FIG. 14A, the surface 1a of the sample is substantially plane and the platen 46 carries out a displacement of the sample 1 and of its surface 1a in two mutually perpendicular directions X and Y parallel to the surface 1a of the sample.

In the case of the device of FIG. 14B, the surface 1a of the sample is substantially cylindrical and the platen 47 carries out a displacement of the sample in rotation Ω about the axis of the cylindrical surface 1a and in translation in the direction X of the generators of the surface 1a, so as to carry out the scanning.

In the case of FIG. 15, the source of radiation 26 is arranged outside the hood 43 and linked to the optical heating means 39 by way of an optical fiber 45.

The hood 43 encloses a set of slaved pivoting mirrors 42 which are driven by control electronics and which allow the displacement of the beams 35 and 36 in a first direction X of the surface 1a of the sample.

The hood 43 is mounted on a platen 49 allowing the displacement of the hood 43 and of the beams 35 and 36 parallel to a direction Y of the surface 1a of the sample perpendicular to the direction X.

Represented in FIG. 16 is a device making it possible to carry out the inspection of the inside surface 1a of a tubular part 1.

All the optical means are arranged inside the hood 43 comprising a transparent port 44, with the exception of the source of laser radiation, which is linked by way of an optical fiber 45 to the optical heating means 39 sited inside the hood 43.

The hood 43 is mounted on a platen 50 allowing its displacement in rotation about the axis of the tubular part 1 so as to carry out the scanning of the inside surface 1a of the part 1 in combination with a set of slaved mirrors 42 driven by control electronics in such a way as to displace the beams 36 in the direction X of the generators of the inside surface 1a of the part 1.

Represented in FIGS. 17A and 17B are two devices all of whose optical elements are arranged inside the hood 43 comprising a transparent exit port 44. The hood 43 is fixed and contains an assembly involving slaved mirrors 52 making it possible to displace the beams 35 and 36 in a direction X of the surface 1a of the sample 1, so as to carry out the scanning.

In the case of the device represented in FIG. 17A, a platen 51 makes it possible to displace the sample 1a in a direction Y perpendicular to the direction X.

In the case of the device represented in FIG. 17B, the part or sample 1 has a cylindrical shape and a platen 53 makes it possible to pivot the part 1 about its axis, so as to carry out the Ω-wise scan in combination with the system involving slaved mirrors 52 displacing the beams 35 and 36 in the direction X which is parallel to the generators of the cylindrical surface 1a of the part 1.

Although a characteristic element of the method and of the device in accordance with the invention is constituted by the use of a matrix of detectors, in certain cases, the matrix of detectors can be reduced to a simple alignment of detectors constituting a strip of detectors.

Represented in FIG. 18A is a first embodiment of a simplified device which includes a simple strip of detectors 19, instead of a matrix of detectors 20.

In this case, an inspection of the surface 1a of the part can be carried out in point mode, the heating 22 and detection 23 zones being realized in point-like form and delivering, in each of their successive positions, one pixel of the image originating from a detector 19' of the strip of detectors 19 in a particular position, the choice of which makes it possible to adjust the offset between the zones 22 and 23, during a linewise scan shown schematically by the arrow 24. In this case, the scan can only be carried out in a single direction and the offset between the heating 22 and detection 23 zones can be adjusted in this direction by choosing the detector 19' of the strip of detectors 19 which is sited parallel to the scan lines.

Represented in FIG. 18B is the surface 1a of a part whose thermographic inspection is carried out in line mode, by using a strip of detectors 19. The heating 22 and detection 23 zones have an elongate shape and detection is carried out on the basis of a line of detectors 19' which is chosen on the strip of detectors 19 which is sited perpendicularly to the direction of scan 24.

In this case, it is possible to adjust the length of the line corresponding to the zones 22 and 23 by adjusting the length of the line of detectors 19' which is chosen from the strip of detectors 19. However, it is not then possible to adjust the amplitude or the sign of the offset between the heating 22 and detection 23 zones.

The method and the device in accordance with the invention therefore make it possible to obtain thermographic images of surfaces of a part of any shape with a reduced duration of execution, thus rendering the method applicable to parts having considerable surfaces.

Furthermore, the method and the device according to the invention make it possible to adapt the offset between the heating zone and the detection zone and the spatial distribution of the laser, in such a way as to obtain, as a function of the geometrical or physical characteristics of the part or of the presence of defects in this part, the most favorable signal/noise ratio possible.

The method and the device according to the invention may be adapted to parts having surfaces of any shape.

The invention applies in general to the thermographic inspection of any part regardless of the constituent material of this part.

What is claimed is:

1. Method for the photo-thermal inspection of a material, comprising:

heating a heating zone at a surface of a part made of the material, by using a heating means, detecting a flux radiated by the surface of the part in a detection zone at a distance from the heating zone, moving said heating means for displacing said heating zone at the surface of the part along a defined scanning path, selecting at least one detector from a set of detectors arranged in relative spaced positions, to receive a flux radiated from the detection zone, said at least one selected detector being selected so as to optimize the photo-thermal inspection and to increase the speed of execution of this inspection;

processing an output signal of the at least one detector; and adjusting the distance between the heating zone and the detection zone by selecting at least one detector in a set of detectors arranged in a line of detectors located in a detector matrix.

2. Method according to claim 1, comprising:

adjusting the value and the sense of the distance displacement between the heating zone and the detection zone by selecting the detector or row of detectors.

3. Method for the photo-thermal inspection of a material, comprising:

heating a heating zone at a surface of a part made of the material, by using a heating means, detecting a flux radiated by the surface of the part in a detection zone at a distance from the heating zone, moving said heating means for displacing said heating zone at the surface of the part along a defined scanning path, selecting at least one detector from a set of detectors arranged in relative spaced positions, to receive a flux radiated from the detection zone, said at least one selected detector being selected so as to optimize the photo-thermal inspection and to increase the speed of execution of this inspection;

processing an output signal of the at least one detector; and adjusting a length of the detection zone, by choosing a number of detectors of a row of detectors selected in the set of detectors.

4. Method for the photo-thermal inspection of a material, comprising:

heating a heating zone at a surface of a part made of the material, by using a heating means, detecting a flux radiated by the surface of the part in a detection zone at some distance from the heating zone, moving said heating means for displacing the heating zone at the surface of the part successively in a first direction and then in a second direction opposite to the first direction, along a defined scanning line, and selecting, from a set of detectors arranged in relative spaced positions to receive a flux radiated from the detection zone, at least one first detector while moving said heating means in the first direction and at least one second detector while moving said heating means in the second direction.

5. Method according to claim 4, comprising modifying the value and the sign of the distance between said heating zone and said detection zone by selecting the at least one second detector between a first displacement of the heating means along the scanning line in the first direction and a second displacement of the heating means along the scanning line in the second direction.

6. Method according to claim 4, comprising selecting the at least one second detector of the set of detectors in such a way that the distance between the heating zone and the detection zone is directed along a line making an angle between 0 and 360°.

7. Method for the photo-thermal inspection of a material, comprising:

heating a heating zone at a surface of a part made of the material, by using a heating means, detecting a flux radiated by the surface of the part in a detection zone at a distance from the heating zone, moving said heating means for displacing said heating zone at the surface of the part along a defined scanning path, selecting at least one detector from a set of detectors arranged in relative spaced positions, to receive a flux radiated from the detection zone, said at least one selected detector being selected so as to optimize the photo-thermal inspection and to increase the speed of execution of this inspection;

processing an output signal of the at least one detector;

providing a set of detectors in the form of a matrix of detectors having the shape of a parallelogram array comprising relatively perpendicular lines and columns of detectors;

selecting a group of detectors of the set of detectors placed along at least one of a line of a matrix;

displacing the heating zone, during scanning, in a direction which is not parallel to lines of the set of detectors constituting a matrix and selecting adjacent detectors of the matrix of detectors which are located along different lines of the matrix of detectors.

8. Method for the photo-thermal inspection of a material comprising:

heating a heating zone at a surface of a part made of the material with a laser beam, detecting a flux radiated by the surface of the part in a detection zone at some distance of the heating zone, said flux being in the form of a detection beam, using optical detection means, moving said laser beam for displacing said heating zone at the surface of the part along a defined scanning path, measuring distances between said optical heating means and said optical detection means as well as between said heating zone and said detection zone, and adjusting the focus of said heating laser beam and said detection beam from the measured distances.

9. Device for the photo-thermal inspection of material comprising a means of heating a heating zone of the surface of a part made of the material, means of detection of a flux radiated by the surface of the part in a detection zone, means of scanning for displacing the heating zone, and the detection zone over the entire surface of the part, and means for processing signals from the means of flux detection for constructing a thermographic image of the surface of the part, and electronic means for selecting at least one detector chosen from a set of detectors constituting a matrix of detectors, said at least one detector constituting the means of detection of the radiated flux; and the means of heating being a laser beam provided by a laser radiation source located in an optical path with optical means making it possible to focus the laser beam originating from the radiation source onto the surface of the part, and wherein the flux radiated by the detection zone of the surface of the part is an infrared radiation whose focusing is effected by focusing means, a meter for measuring the distance between the optical means for focusing the laser beam and the surface of the part, and for measuring the distance between the means of focusing the infrared radiation and the surface of the part, and means of real-time slaving of the optical focusing means to the distance measurements.

10. Device in accordance with claim 9, wherein the laser radiation source is linked to the optical focusing means by an optical fiber.

11. Device for the photo-thermal inspection of material comprising a means of heating a heating zone of the surface of a part made of the material, means of detection of a flux radiated by the surface of the part in a detection zone, means of scanning for displacing the heating zone, and the detection zone over the entire surface of the part, and means for processing signals from the means of flux detection for constructing a thermographic image of the surface of the part, and electronic means for selecting at least one detector chosen from a set of detectors constituting a matrix of detectors, said at least one detector constituting the means of detection of the radiated flux; and the means of heating the heating zone being a laser beam provided by a laser radiation source associated with optical means for focusing the laser beam originating from the laser radiation source onto the surface of the part, and wherein the flux radiated by the detection zone of the surface of the part is an infrared radiation focused by focusing means, a meter for measuring the distance between the optical means for focusing the laser beam and the surface of the part and for measuring the distance between the means for focusing the infrared radiation and the surface of the part, and means for storing in a memory the distances measured by the meter during scanning of the surface of the part and of controlling the means of focusing in non-real time on the basis of the distances stored in memory.

12. Device for the photo-thermal inspection of material comprising a means of heating a heating zone of the surface of a part made of the material, means of detection of a flux radiated by the surface of the part in a detection zone, means of scanning for displacing the heating zone, and the detection zone over the entire surface of the part, and means for processing signals from the means of flux detection for constructing a thermographic image of the surface of the part, and electronic means for selecting at least one detector chosen from a set of detectors constituting a matrix of detectors, said at least one detector constituting the means of detection of the radiated flux; and wherein the means of scanning comprise optical means and means for mechanically displacing the part.

13. Device for the photo-thermal inspection of material comprising a means of heating a heating zone of the surface of a part made of the material, means of detection of a flux radiated by the surface of the part in a detection zone, means of scanning for displacing the heating zone, and the detection zone over the entire surface of the part, and means for processing signals from the means of flux detection for constructing a thermographic image of the surface of the part, and electronic means for selecting at least one detector chosen from a set of detectors constituting a matrix of detectors, said at least one detector constituting the means of detection of the radiated flux; and wherein the means of scanning comprise optical means and also means for mechanically displacing a means for providing a laser beam for heating the surface of the part and for mechanically displacing reception of the flux radiated by the detection zone of the surface of the part.

14. Device for the photo-thermal inspection of material comprising a means of heating a heating zone of the surface of a part made of the material, means of detection of a flux radiated by the surface of the part in a detection zone, means of scanning for displacing the heating zone, and the detection zone over the entire surface of the part, and means for processing signals from the means of flux detection for constructing a thermographic image of the surface of the part, and electronic means for selecting at least one detector chosen from a set of detectors constituting a matrix of detectors, said at least one detector constituting the means of detection of the radiated flux; and a semi-reflecting plate for deflecting a heating beam towards the surface of the part and for transmitting the flux radiated by the detection zone of the surface of the part to the detection means.

15. Device for the photo-thermal inspection of material comprising a means of heating a heating zone of the surface of a part made of the material, means of detection of a flux radiated by the surface of the part in a detection zone, means of scanning for displacing the heating zone, and the detection zone over the entire surface of the part, and means for processing signals from the means of flux detection for constructing a thermographic image of the surface of the part, and electronic means for selecting at least one detector chosen from a set of detectors constituting a matrix of detectors, said at least one detector constituting the means of detection of the radiated flux; and wherein the heating means is a radiation source associated with optical means of focusing, and wherein the optical means of focusing spread the radiation of the source selectively along a straight line or elongated ellipse of adjustable length and orientation.

* * * * *